United States Patent [19]
Walker et al.

[11] Patent Number: 5,474,774
[45] Date of Patent: Dec. 12, 1995

[54] ADHESION INHIBITING COMPOSITION

[75] Inventors: Edward B. Walker; Richard A. Mikelsen, Jr.; Jennifer N. Mickelsen; Brent L. Roth, all of Ogden, Utah

[73] Assignee: JLB, Inc., Ogden, Utah

[21] Appl. No.: 218,504

[22] Filed: Mar. 25, 1994

[51] Int. Cl.$^6$ .................................................. A61K 35/78
[52] U.S. Cl. ........................ 424/195.1; 514/449; 514/451; 514/783
[58] Field of Search .......................... 424/195.1; 514/783

[56] References Cited

U.S. PATENT DOCUMENTS

| | | | |
|---|---|---|---|
| 3,963,700 | 6/1976 | Philip | 260/236.5 |
| 4,083,779 | 4/1978 | Combe et al. | 210/23 H |
| 4,309,207 | 1/1982 | Devlin | 71/79 |
| 4,652,448 | 3/1987 | Sadowski | 424/87 |
| 4,775,477 | 10/1988 | Stahl et al. | 210/641 |
| 4,857,327 | 8/1989 | Virdalm | 424/195.1 |
| 5,128,100 | 7/1992 | Hollis et al. | 422/14 |
| 5,200,186 | 4/1993 | Gabetta et al. | 424/195.1 |

FOREIGN PATENT DOCUMENTS

| | | |
|---|---|---|
| 3027933 | 2/1981 | Germany . |
| 3427014 | 1/1986 | Germany . |

OTHER PUBLICATIONS

Fuleki et al. *J. Food Science* vol. 33, pp. 266–274, (1968).
Fuleki et al. *J. Food Science* vol. 32, pp. 527–530, (1967).
Fuleki et al. *J. Food Science* vol. 33(1), pp. 72–77, (1968).
Wang et al. *J. Food Science* vol. 43(5), pp. 1402–1404, (1978).

*Primary Examiner*—Douglas W. Robinson
*Assistant Examiner*—Howard C. Lee
*Attorney, Agent, or Firm*—Trask, Britt & Rossa

[57] ABSTRACT

An extract prepared from plants of the genus Vaccinium, especially cranberries, which is enriched for an activity which inhibits bacterial adhesion to surfaces. The extract is also enriched for polyphenol and flavonoid compounds, lacks detectable amounts of simple sugars, has a very low content of benzoic acid relative to raw cranberries, and lacks significant amounts of anthocyanins. Methods for preparing and for using the extract are also disclosed.

1 Claim, 16 Drawing Sheets

5,474,774

ADHESION INHIBITING COMPOSITION

BACKGROUND OF THE INVENTION

1. Field

The invention relates to plant extracts having therapeutic and other uses, and more particularly to an extract of cranberries.

2. State of the Art

It is presently believed that cranberry juice or some fraction thereof inhibits the adhesion of bacteria to mammalian cells, particularly epithelial cells. This property of anti-adhesion can be applied to industrial uses, such as the cleaning of vats from bacterial fermentation, cleaning of medical and dental instruments, cleaning of dishes or tools used in sterile laboratory procedures, and the like.

Many persons also consider cranberry juices and cranberry derivatives to be beneficial to health, and products including powders made from cranberries or cranberry juices are available commercially. Doctors often recommend cranberry products for female patients suffering from urinary tract infections. However, most available preparations, as well as raw cranberries and typical cranberry juice products have a relatively high acidity due in part to the amount of benzoic acid present. The acidity can cause stomach upset, stimulate tooth decay, and produces a sour taste which is unappealing to many persons.

Consequently, a need remains for a cranberry extract which includes the active fraction of cranberries responsible for the anti-bacterial adhesion activity. A need also remains for a composition in which the active fraction is concentrated and/or partially purified to have a higher anti-adhesion activity per weight unit. It would furthermore be highly desirable to provide reliable markers for identifying the active fraction during a concentrating or purifying process. A need also remains for a cranberry extract which contains the active fraction but has substantially reduced acidity and sugar content.

SUMMARY OF THE INVENTION

The invention comprises an extract made from plant material of plant species of the genus Vaccinium, and which is significantly enriched for an activity that interferes with adhesion of bacterial cells to surfaces. The extract is also enriched for polyphenol and flavonoid compounds including ones having a glycoside moiety. When the extract is analyzed by reverse-phase HPLC on a C18 lipophilic column, characteristic sets of elution peaks of compounds absorbing at 230 nm, 280 nm and 360 nm are observed. The extract may also contain tannin compounds represented by elution peaks absorbing in the ultraviolet wavelength region.

In the presently preferred embodiment, the extract is enriched by at least about 500- to 1500-fold for the anti-adhesion activity, as compared with juices which are 100% derived from the plant material. The extract is enriched to a similar degree in the concentration of flavonoid and other polyphenol compounds detected by spectroscopic methods.

In a currently preferred embodiment, the extract is very low in acid and in simple sugars, with a benzoic acid content typically less than about 0.01 milligrams per gram dry powder, and essentially undetectable amounts of free monomer or dimer sugars. The preferred embodiment is prepared from cranberries (*V. macrocarpon* and variants). However, other useful species are *V. myrtilis* (bilberry), *V. oxycoccus* (European cranberry), and *V. corymbosum* (blueberries).

The invention also includes a method of making an extract having the properties outlined in the preceding paragraphs, and a method of inhibiting the adhesion of bacteria to surfaces using the extract.

The presently preferred method of making the extract includes at least the steps of: preparing a starting extract from plants or plant parts of species selected from the genus Vaccinium, this starting extract including charged and polar compounds and the active fraction; concentration of the extract to a smaller volume; and enrichment of the extract for the active fraction and for polyphenol and flavonoid compounds generally. In a presently preferred embodiment, the method includes the further steps of: removing most of the free monomer and dimer sugars from the extract; removing most of the benzoic acid from the extract; removing anthocyanins. Steps following the preparation of a starting extract, are not necessarily performed in the order listed. Techniques are described for accomplishing each of the indicated steps by chromatography or by precipitation and phase extraction steps. Additionally, in one embodiment the method includes a step of mannose affinity chromatography which selects for compounds that can compete for binding to a mannose-affinic substrate.

The invention further embraces compositions produced by first extracting non-active compounds from plant materials with a basic (high pH) solution, leaving a pulp or residue enriched for the anti-adhesion active fraction. This pulp or residue may be further processed by acid solubilization followed by selected steps as described in the preceding paragraphs, to further enrich for the active fraction.

The anti-adhesion property of the extract is useful in a number of areas, for example the cleaning of industrial fermentation equipment, medical and dental instruments, laboratory culture jars, and the like. The extract may further have usefulness to inhibit the adhesion of bacteria to surgical implants, to tooth surfaces and oral cell types found in the mouth, and to cells in the urinary tract of humans and/or animals. The presently preferred extract has a greatly reduced content of both acids and sugar, and is an excellent food supplement to replace cranberries and cranberry juice. The low sugar and acid content make the extract highly suitable for oral hygiene products, and more useful to those who seek the health benefits of a cranberry extract product.

A method of inhibiting the adhesion of bacteria comprises the steps of providing an extract as described, applying the extract in a suitable medium to a surface(s) having bacteria such as *E. coli* adhered thereto, to disengage the bacteria from the surface(s). The method is useful to inhibit the adhesion of bacteria to such surfaces as teeth, other bacteria adhered to teeth, to human oral epithelial cells, human epithelial urinary tract cells; and to clean dental implants, bacterial fermentation vats, and the like.

BRIEF DESCRIPTION OF THE DRAWINGS

In the drawings, which illustrate what is presently regarded as the preferred embodiment.

DETAILED DESCRIPTION OF THE ILLUSTRATED EMBODIMENT

An extract of species of the genus Vaccinium which is highly enriched for an active fraction having activity to inhibit the adherence of certain bacterial species to various substrates, is also highly enriched in the content of flavonoids and polyphenols. The extract may be in powder form or in solution in a suitable solvent. The powdered form is a reddish-brown powder with a density of about 0.43±0.03 gm/cubic centimeter and other properties as described in the subsequent paragraphs. For convenience and clarity, the extract will be referred hereinafter as the "enriched extract", or, when reference is made to an extract made from a particular species such as cranberries, as the "cranberry extract".

Table I shows the solubility of one embodiment of a powder according to the invention, in various solvents of differing degrees of polarity.

The refractive index of an aqueous solution of the powder is about 1.3320 at a concentration of 1.0 mg/ml, and about 1.3370 at a concentration of 8.5 mg/ml (the maximum solubility in water).

TABLE I

| Solvent | Solubility |
| --- | --- |
| Acetone | 133 mg/ml |
| Methanol | 530 mglml |
| Ethanol | 450 mg/ml |
| Butanol | 275 mg/ml |
| Water | 8.5 mg/ml |

Figure 2:
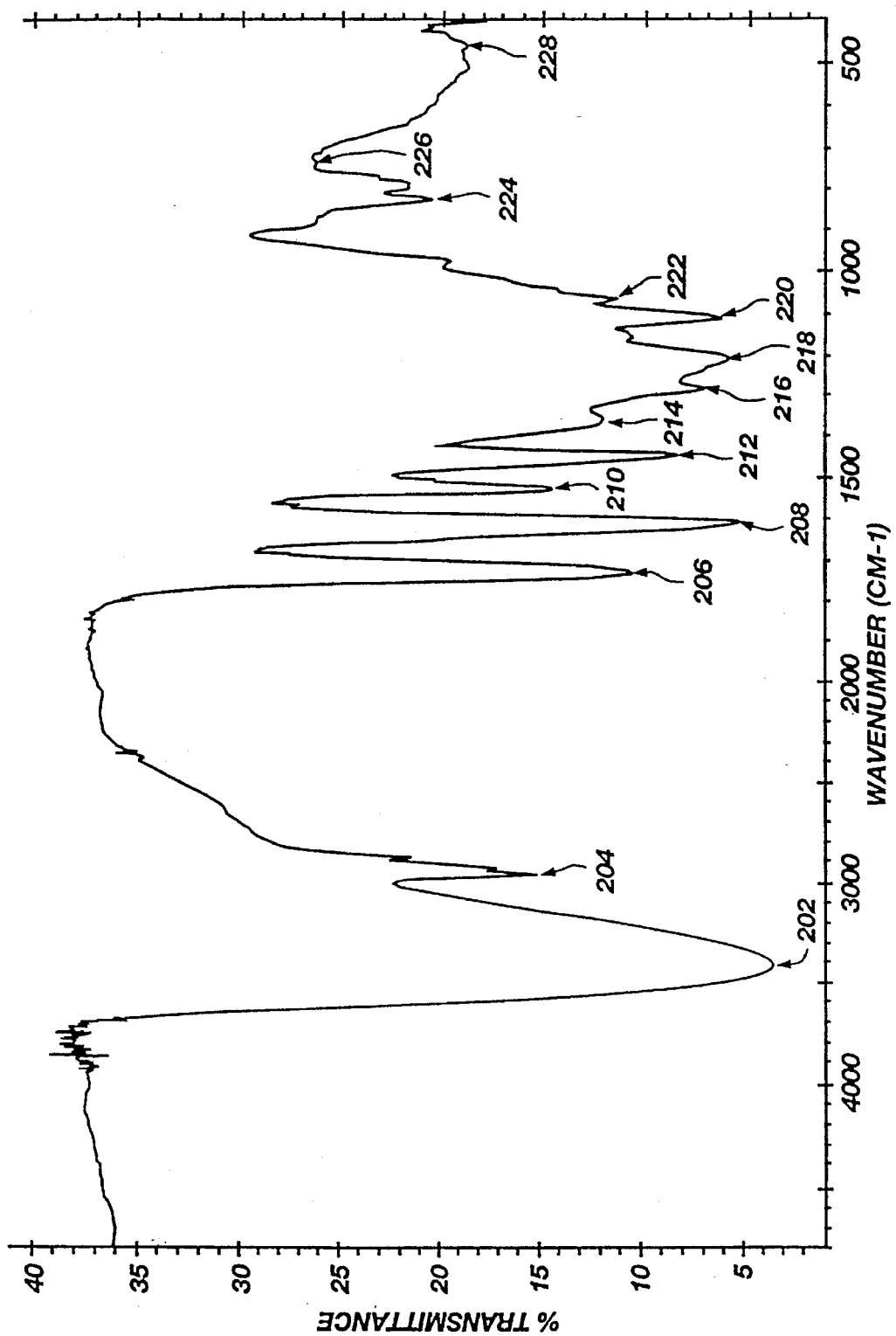
FIG. 2 is an infrared absorbance spectrum of the extract dissolved in water.

The extract prepared from cranberries (berries of *V. macrocarpon*) has certain characteristics observable in absorbance spectra in the infrared, visible and ultraviolet light ranges. FIG. 2 shows an infra-red transmittance spectrum of the extract, with significant absorbance troughs at approximately the following respective wave numbers in $cm^{-1}$: 3410, 2960, 1735, 1610, 1524, 1443, 1360, 1285, 1210, 1111, 1066, 822, 785, 500, which are respectively indicated by reference numerals 202, 204, 206, 208, 210, 212, 214, 216, 218, 220, 222, 224, 226, 228. Peak 228 at about 500 $cm^{-1}$ is very broad.

Figure 3:
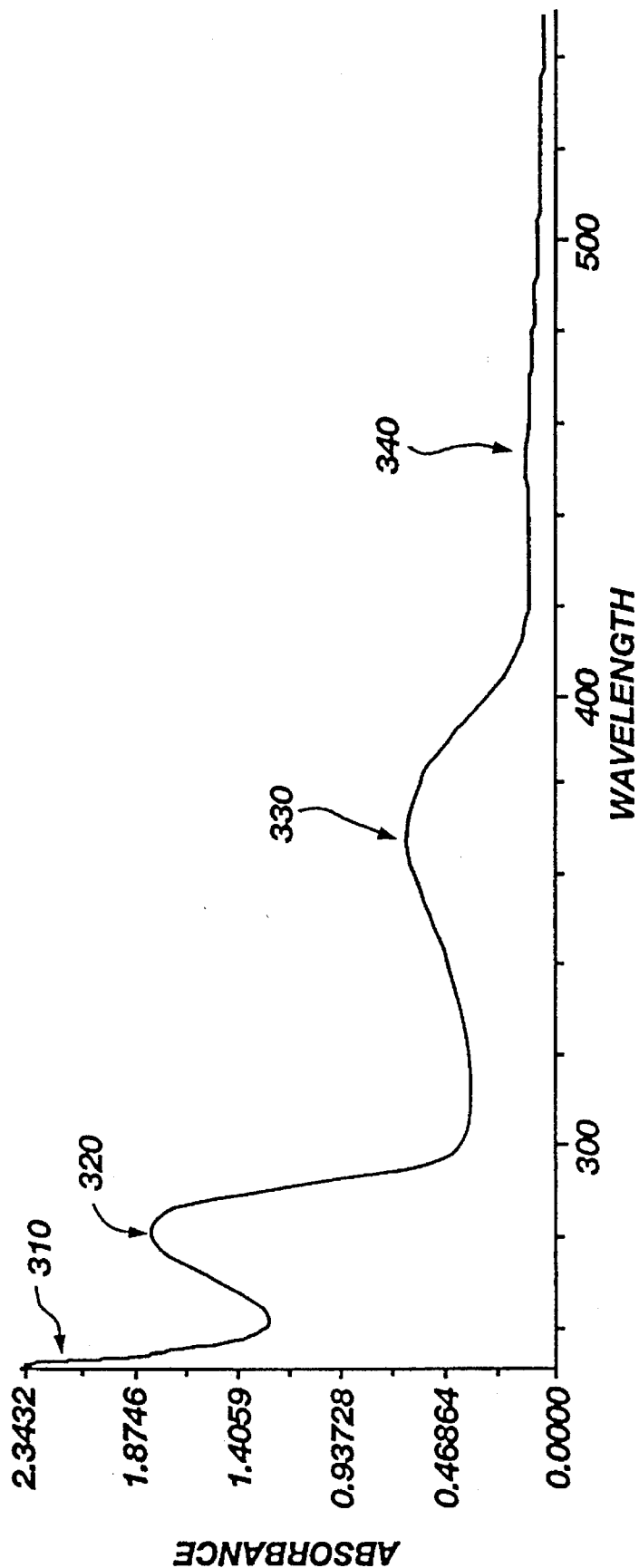
FIG. 3 is an ultra-violet/visible light absorbance spectrum of the extract dissolved in methanol.

FIG. 3 shows an absorption spectrum of the cranberry extract dissolved in methanol, for wavelengths from about 250 nanometers (hereafter abbreviated "nm") through about 600 nm (the ultraviolet and visible light regions). The concentration of the extract in methanol is about 0.05 mg/ml. Four major absorption peaks at wavelengths of about 202, 278, 368, and 454 nanometers, are respectively indicated by arrows 310, 320, 330, 340. These three peaks appear to be characteristic of the extract. The relative intensities of the peaks may be somewhat variable, but are generally in the range of about 1.8:0.64:0.12 respectively for the peaks 310, 320, 330, 340. Polyphenols, including flavonoid-containing compounds, are known to have UV/visible light absorbance spectra with similar features.

Figure 4:
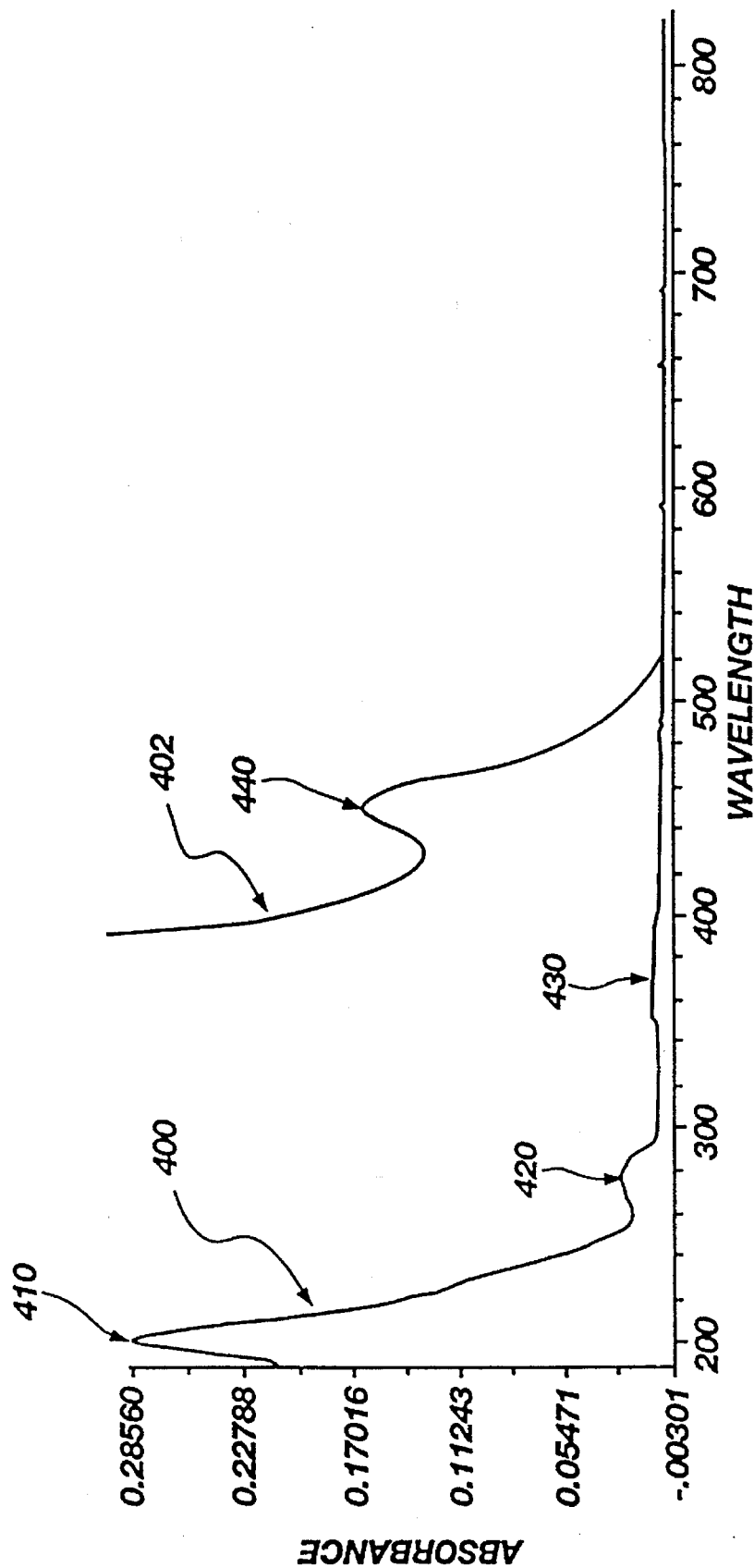
FIG. 4 is an ultra-violet/visible light absorption spectrum of the extract dissolved in water.

FIG. 4 depicts absorption spectra of the invented cranberry extract dissolved in water, at two different concentration levels (curves 400, 402). Curve 402 is taken from a sample which is 200 times more concentrated than that of curve 400. The spectrum has the following characteristic absorbance peaks: 202 nm, 278 nm, 368 nm, and 454 nm, which are indicated respectively by reference numerals 410, 420, 430 and 440. The approximate relative intensities of the peaks are, in $(mg/ml)^{-1}(cm)^{-1}$, 42, 1.1, 0.3, and 3.6, respectively. Peaks Nos. 420, 430 (278 nm and 368 nm, respectively) are also characteristic of the spectra in water of flavonoid- and polyphenol-containing compounds. Generally, an absorbance at both 280 nm and 360–370 nm is indicative of the presence of flavonoids, whereas polyphenols have the greatest absorbance in the 200 nm to 280 nm range and exhibit little or no absorbance at 360–370 nm.

The flavonoid/polyphenol compounds present in the extract include compounds having a glycoside moiety. Several flavonoid compounds lacking a glycoside moiety, including myricetin, rutin, and quercetin, have been tested and found not to have anti-adhesion activity.

Figure 5A:
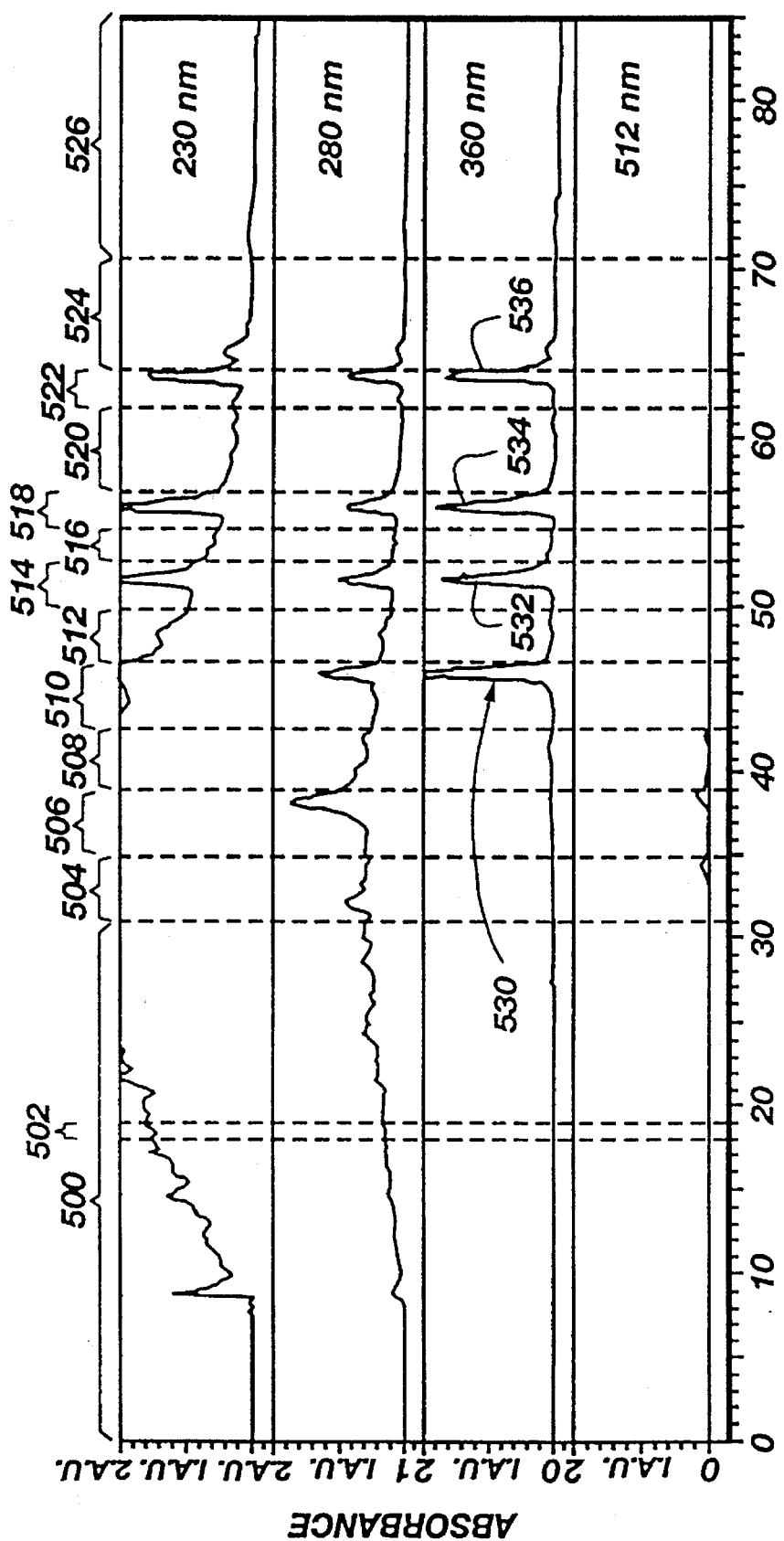
FIGS. 5A–5B depicts a comparative analysis of a high-pressure liquid chromatogram of the extract by absorbance at wavelengths of 230 nm, 280 nm, 360 nm and 512 nm.
Figure 6B:
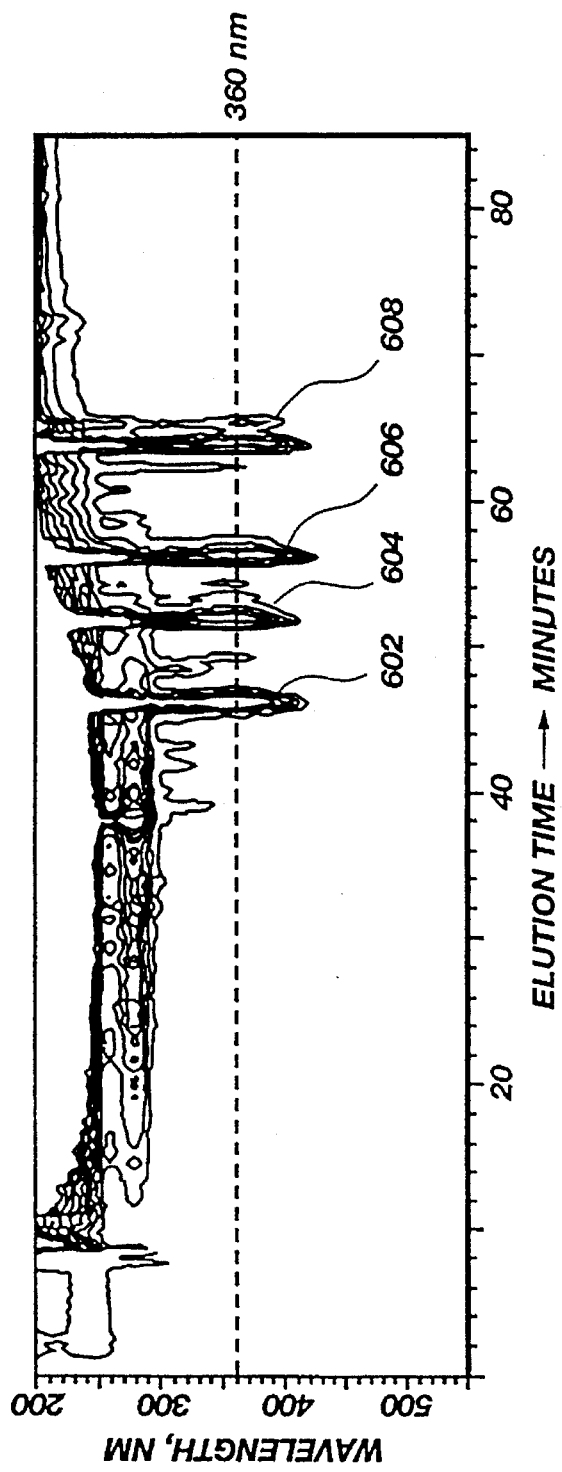
FIGS. 6A–6B is a chart depicting a dual spectral analysis and analysis of elution peaks absorbing at 360 nm, of a high-pressure liquid chromatogram of the extract.
Figure 6A:
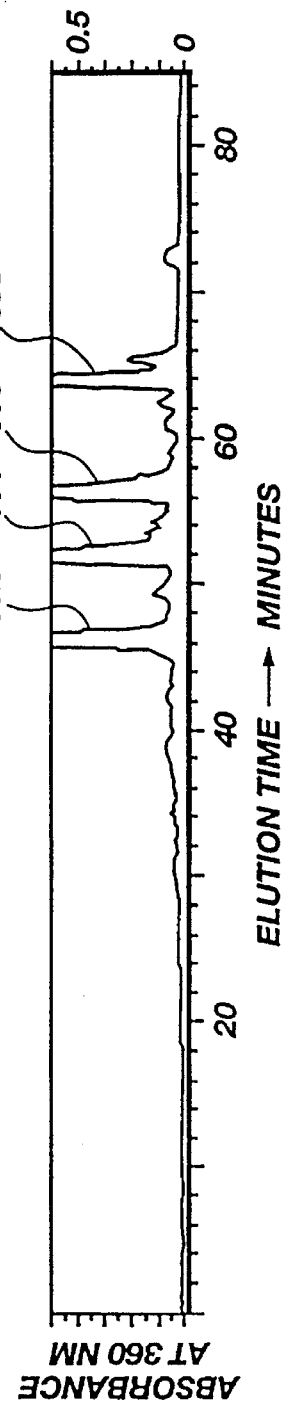
Figure 7A:
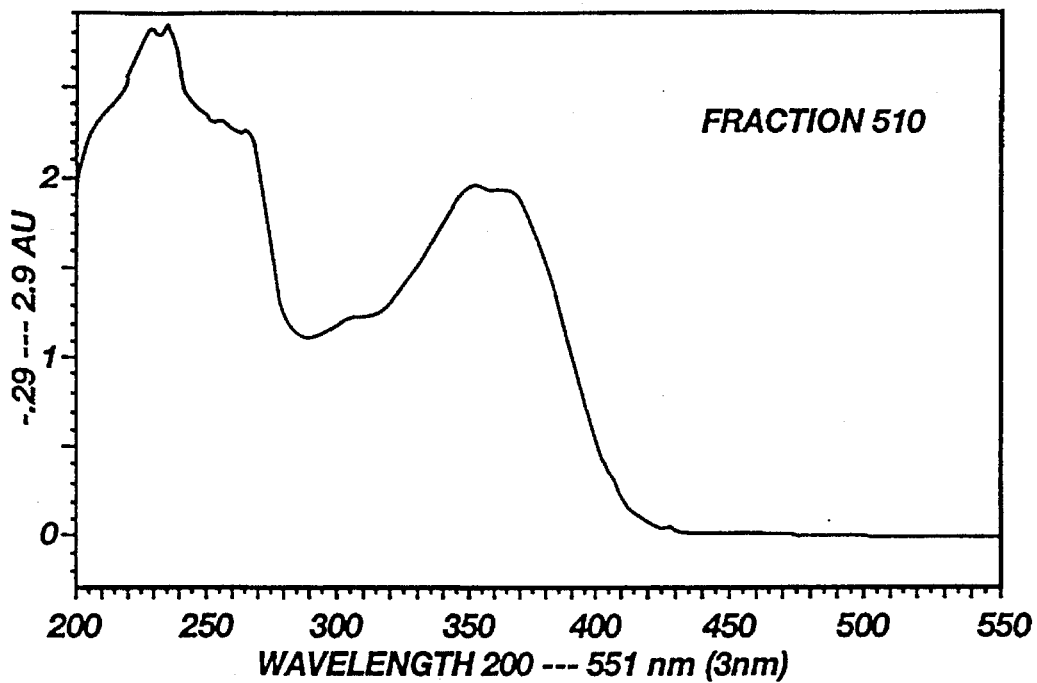
FIGS. 7A–7F contains charts depicting the complete UV-visible light spectra of selected HPLC fractions taken from the sample whose chromatogram is shown in FIGS. 5A–5B.
Figure 7B:
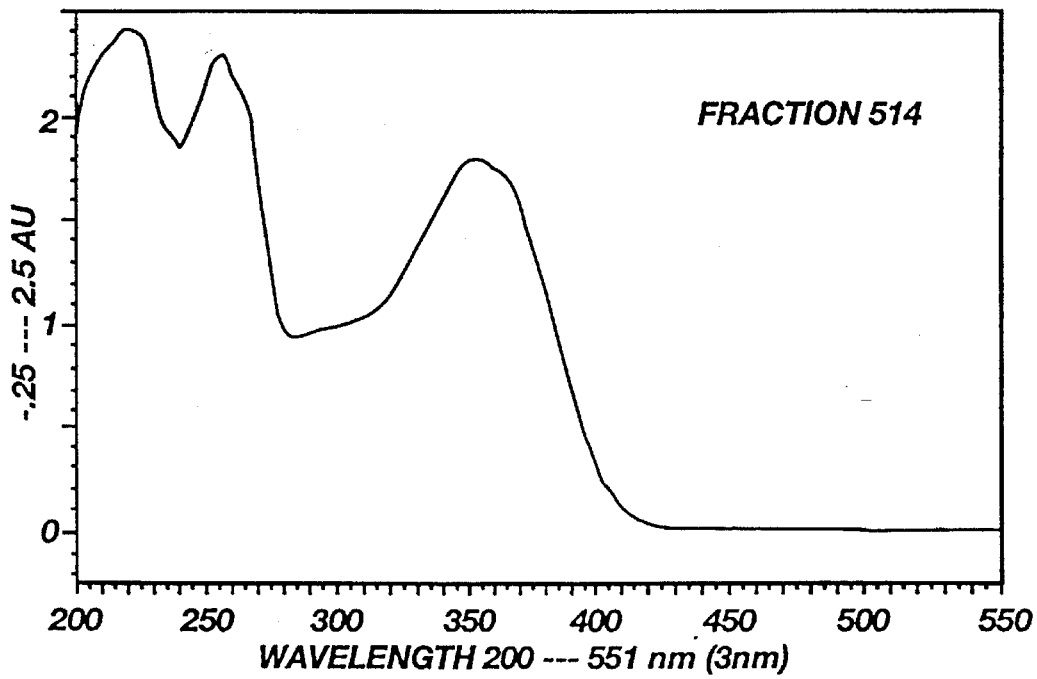
Figure 7C:
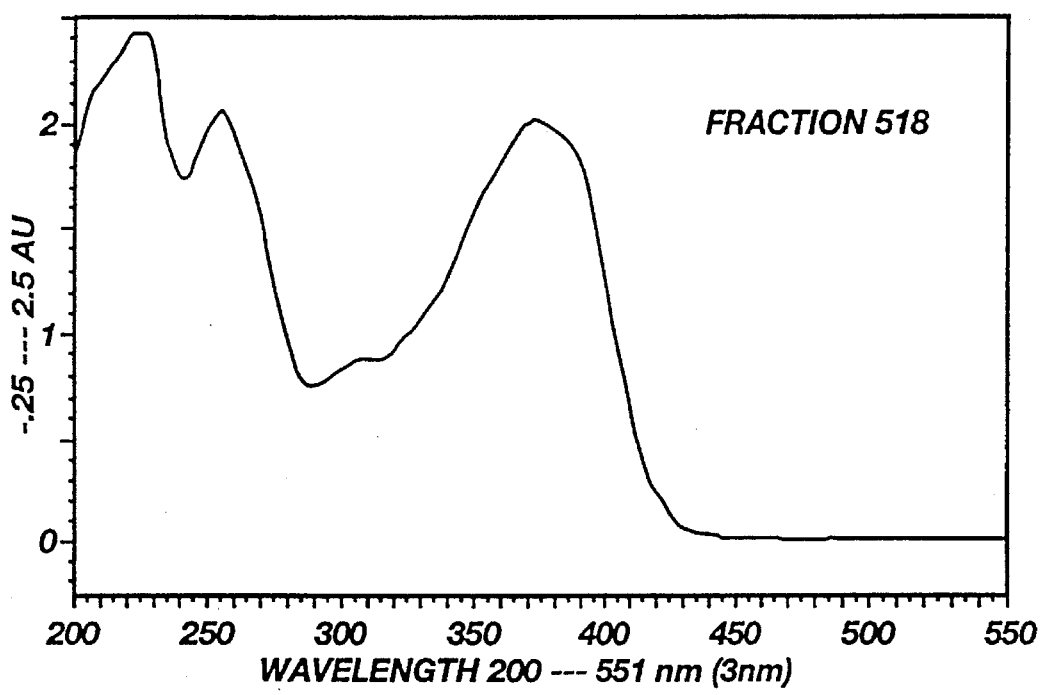
Figure 7D:
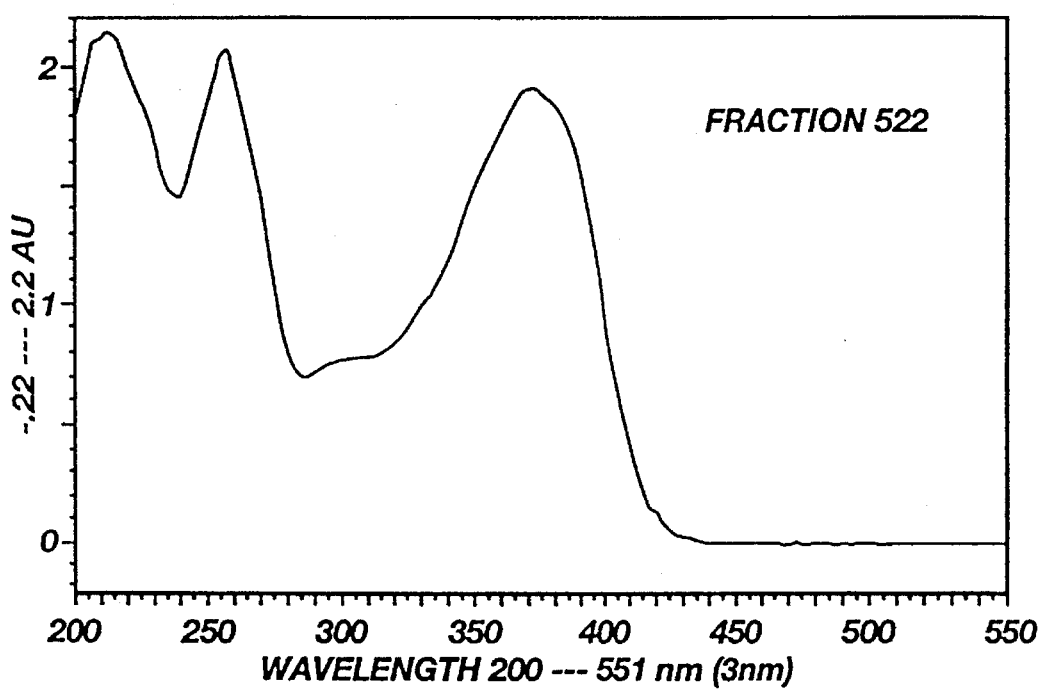
Figure 7E:
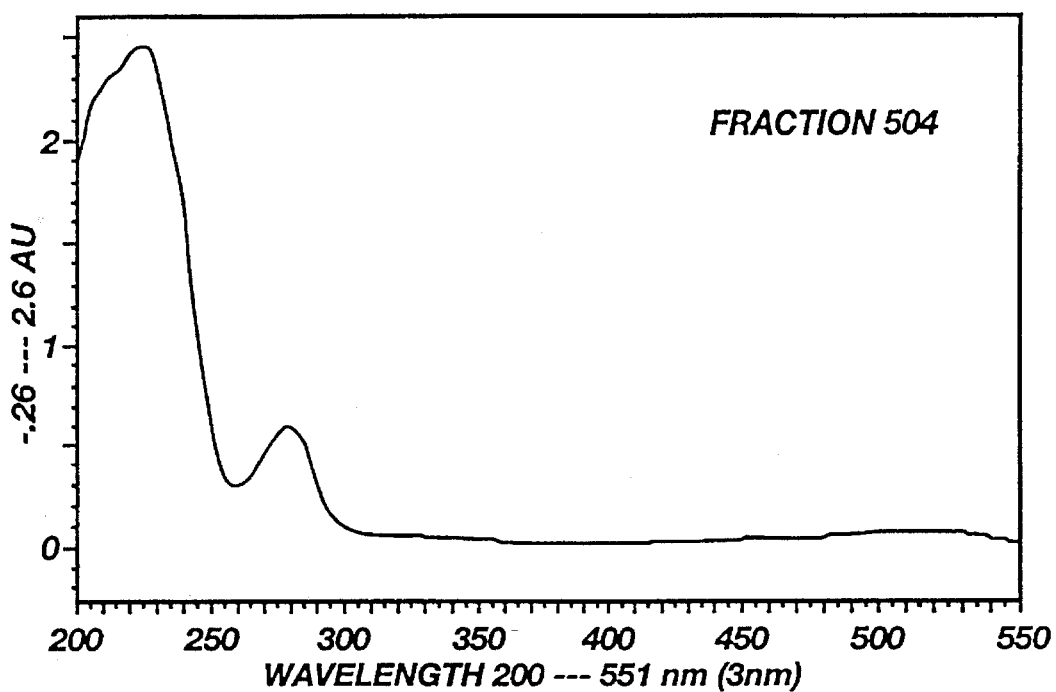
Figure 7F:
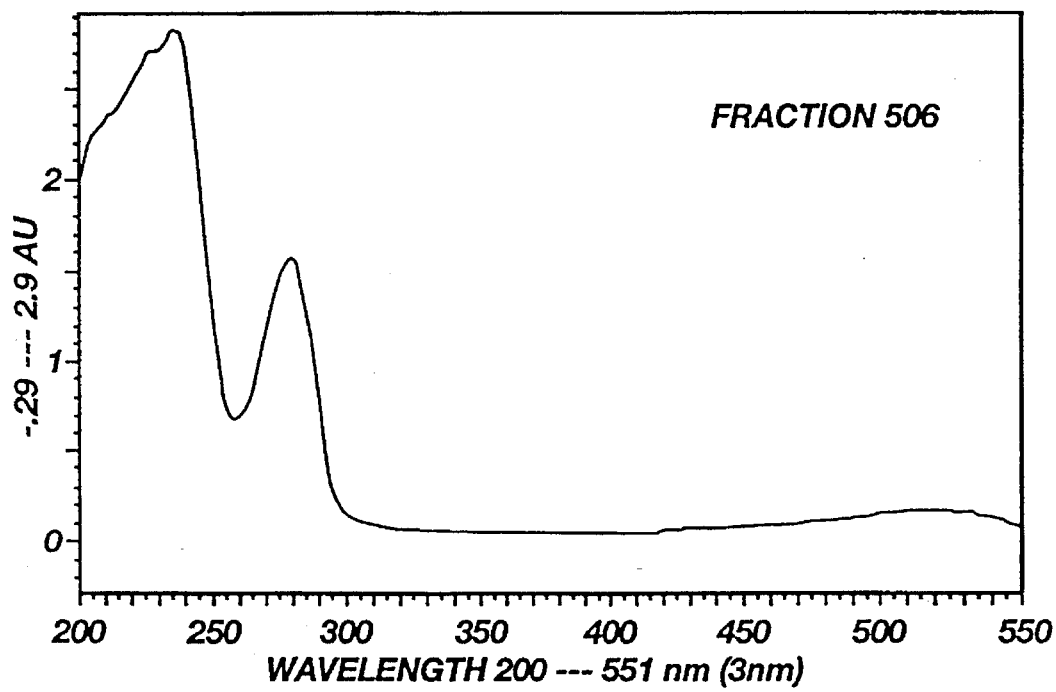

The cranberry extract is also characterized by the elution at specific times during high-pressure liquid chromatography (HPLC) of the extract dissolved in methanol, of 360 nm light-absorbing components. FIGS. 5A and 6A depict typical elution vs. time chromatograms of the cranberry extract of components which absorb at 360 nm. Fifteen hundred microliters of a solution containing 100 milligrams of dry powder per 4 milliliters of methanol (25 mg/ml; about 37.5 mg) was applied to a preparative-size reverse phase C18 column (Waters C18 prepacked column, BONDAPAK, cat. #WAT038505, Millipore Corp., Waters Chromatography, 34 Maple St., Milford Mass. 01730). The C18 is a lipophilic affinity agent having carbon chains 18 carbons in length bound to the beads. For a preparative size column of about 50 ml volume, 25 mm diameter and 100 mm length, a two-solvent linear gradient from 80% A/20% B (A=0.4% phosphoric acid, B=methanol) to 31% A/69% B is run at a flow rate of 5 ml/minute over a time from 0 to 76 minutes. After 76 minutes, an isocratic flow at 31% A/69% B is maintained for an additional 44 minutes. With photodetection at 360 nm, about four large 360-nm absorbing peaks are observed respectively at about 46 minutes, 52 minutes, 56 minutes and 64 minutes (identified by reference numerals 602, 604, 606, 608, respectively, in FIG. 6).

For an analytical column of about 5 ml volume (FIG. 8), about 1.25 mg powder is loaded in a volume of about 50 μl. A two-solvent linear gradient from 80% A/20% B (A=0.4% phosphoric acid, B=methanol) to 31% A/69% B is run at a flow rate of 1 ml/min over a time from 0 to 38.3 minutes.

After 38.3 minutes, an isocratic flow at 31% A/69% B was maintained for an additional 21.7 minutes. With photodetection at 360 nanometers, about four major elution peaks are observed at elution times between about 22 minutes and about 40 minutes, and three smaller elution peaks appear earlier, at between about 9 minutes and about 15 minutes.

In some cases (FIG. 9), a 50 ml preparative column was first run for five minutes at 80% A, followed by the linear gradient from 80% A to 31% A over the next 38.3 minutes, and finally by an isocratic phase at 31% A for the succeeding 21.7 minutes (total time 65 minutes). With this gradient protocol, the pattern of 360 nm-absorbing elution peaks associated with the active fraction of the extract is somewhat different, but closer to that observed for the analytical column.

The cranberry extract is also characterized by certain UV-fluorescing components migrating in a specific pattern in paper and thin-layer chromatography (TLC). When a solution of the cranberry extract is subjected to TLC on silica gel in a 98:2 acetone:water solvent, four characteristic fluorescing bands may be observed under long-wave ultraviolet light. These characteristic bands have the properties as described in Table II:

TABLE II

Relative migration distance ($R_f$) and color upon irradiation with ultraviolet light for characteristic bands observed by thin-layer chromatography in acetone:water (98:2).

| | Rf | Color |
|---|---|---|
| Band #0 | 0.0 | faint red |
| Band #1 | 0.2 | blue/blue-white |
| Band #2 | 0.6 | bright yellow |
| Band #3 | 0.7 | bright yellow |
| Band #4 | 0.97 | white |

TABLE III

Relative migration distance ($R_f$) and color of fluorescent bands observed upon irradiation with long-wave ultraviolet light, for paper chromatography in 6:1:2 butanol:acetic acid:water.

| | Rf | Description |
|---|---|---|
| Band #5 | 0.44 | Strong fluorescent yellow |
| Band #6 | 0.50 | faint fluorescent yellow |
| Band #7 | 0.77 | medium fluorescent yellow |

When subjected to paper chromatography on a Whatman #3 paper with a solvent system of 6:1:2 butanol:acetic acid:water, three significant fluorescent peaks are observed on exposure to long-wave (366 nm) UV light. These three peaks are described in Table III.

In a preferred embodiment, the extract (whether from cranberries or other Vaccinium species) is substantially free of free simple sugars (monomer and dimer sugars such as fructose, galactose, glucose, sucrose, etc).

In a further embodiment, the total acid content of the extract (including benzoic acid) is less than about 2%. Benzoic acid is usually present at less than about 0.005 mg per gram. This benzoic acid content is $\leq$ about 1% of that found in certain existing products, as summarized in Table III. Juice products were reduced to a powder before testing and the acid content is given in relation to the weight of the resulting solids.

TABLE IV

| Product | Wt. % Benzoic Acid |
|---|---|
| Knudsen cranberry juice | 0.50 |
| Hains cranberry juice | 0.11 |
| Janet Lee cranberry juice | 0.06 |
| Ocean Spray cranberry cocktail | 0.10 |
| Ocean Spray cranberry powder | 0.12 |
| Cranberry extract of application | 0.0002 |

The reduced content of benzoic acid and total acid results in a product with a less sour taste and which is less likely to cause stomach upset or promote tooth decay.

The cranberry extract having the foregoing properties including a very low content of simple sugars and benzoic acid, has been found to interfere with adherence of bacterial cells to certain cell types, as well as to surfaces such as polystyrene. Examples 1–3 following, demonstrate the anti-adherence properties of the extract.

At least three modes of bacterial cell adherence to other cells and surfaces are known. One mode is mediated by type 1 pili on the surface of the bacteria, and is characterized by sensitivity to free mannose. A second mode is mediated by P-type pili. The mechanisms of the third mode and other adherence modes, are not well-characterized. Guinea pig RBCs are believed to have receptors for the type 1 (mannose-sensitive) pili of *E. coli,* since the bacteria are capable of agglutinating guinea pig RBCs in the absence of mannose but not in its presence (see for example Aronsen, *J. Infect. Dis.* 139:329–332, 1979; Riegman, *J. Bacter.* 172:1114–1120, 1990; Jann, *Infect. Immun.* 22:247–254, 1981).

EXAMPLE #1

Anti-adherence activity measured as interference with bacterial adherence to bladder cells:

Human bladder epithelial cells are collected by centrifugation from the urine of a healthy female volunteer. The cells are washed in standard saline citrate (SSC) and resuspended to the desired volume. The optical density of the cell solution and cell counts are determined. *E. coli* bacterial strains isolated from urinary tract infections are cultured in tryptic soy broth at 37° C. for 72 hours to encourage piliation. The bacteria are also harvested by centrifugation, resuspended in the desired volume of SSC, and the approximate cell number determined.

A test tube is prepared containing 0.667 ml of a selected dilution of the substance to be tested for anti-adherence activity, plus 0.334 ml of the bacterial suspension. The bacteria are incubated with the test substance for 15 minutes at 37° C. Next, 1.0 ml of the bladder cell suspension is added to each tube and the tubes are incubated for a further 15 minutes. Cranberry extract was used in an 8.5 mg/ml solution. Unfractionated cranberry juice was also tested.

After incubation, the content of each tube is filtered through an 8 micron polycarbonate filter, and the filter is rinsed with two volumes (2 ml=one volume) of SSC to wash free any bacteria which are not adhered to the bladder cells. The filter is placed face down on a microscope and the cells are heat-fixed to the slide. The filter is removed, the slides are stained to visualize the cells, and the number of bacteria adhering per cell is counted for each of 20 cells per slide.

Two control tests are also performed. One, the bladder cells are incubated only in SSC without any bacterial suspension or test substance, to determine how many bacteria originating in the urine sample are attached to the epithelial cells. Second, SSC is substituted for the test substance to determine the maximum number of bacteria that adhere to the cells without any inhibitor.

EXAMPLE #2

The following test was developed and used to test the ability of the extract to inhibit agglutination of guinea pig RBCs by *E. coil*:

Red blood cells (abbreviated RBCs) from guinea pigs, purchased from Microbio Products (Tempe, Ariz.) as a suspension in Alsevers solution, are washed in SSC (standard sodium citrate, as known in the art) and resuspended in SSC. Human red blood cells are obtained by standard methods from the blood of volunteers and also prepared by washing and resuspending in SSC. Human RBCs are believed to have a receptor for mannose-resistant pili of *E. coil*.

*E. coil* cultured and prepared as described in the previous example are tested as follows. A series of dots containing graded amounts of the test substance diluted in SSC, plus one dot containing SSC only, are placed on a polystyrene plate. The dots may have a volume of about 10 μl. An equal volume of bacterial suspension is mixed into each dot, followed by ½ volume of RBCs. The total volume in each dot, for a starting volume of 10 μl per dot, is thus 25 μl. The contents of each dot are thoroughly mixed and the degree of agglutination is scored on a scale of 0–4, with 0 representing no agglutination. The sum of the dots at different dilutions is totalled and subtracted from 32 to provide an Activity Index of activity interfering with agglutination.

Figure 5B:
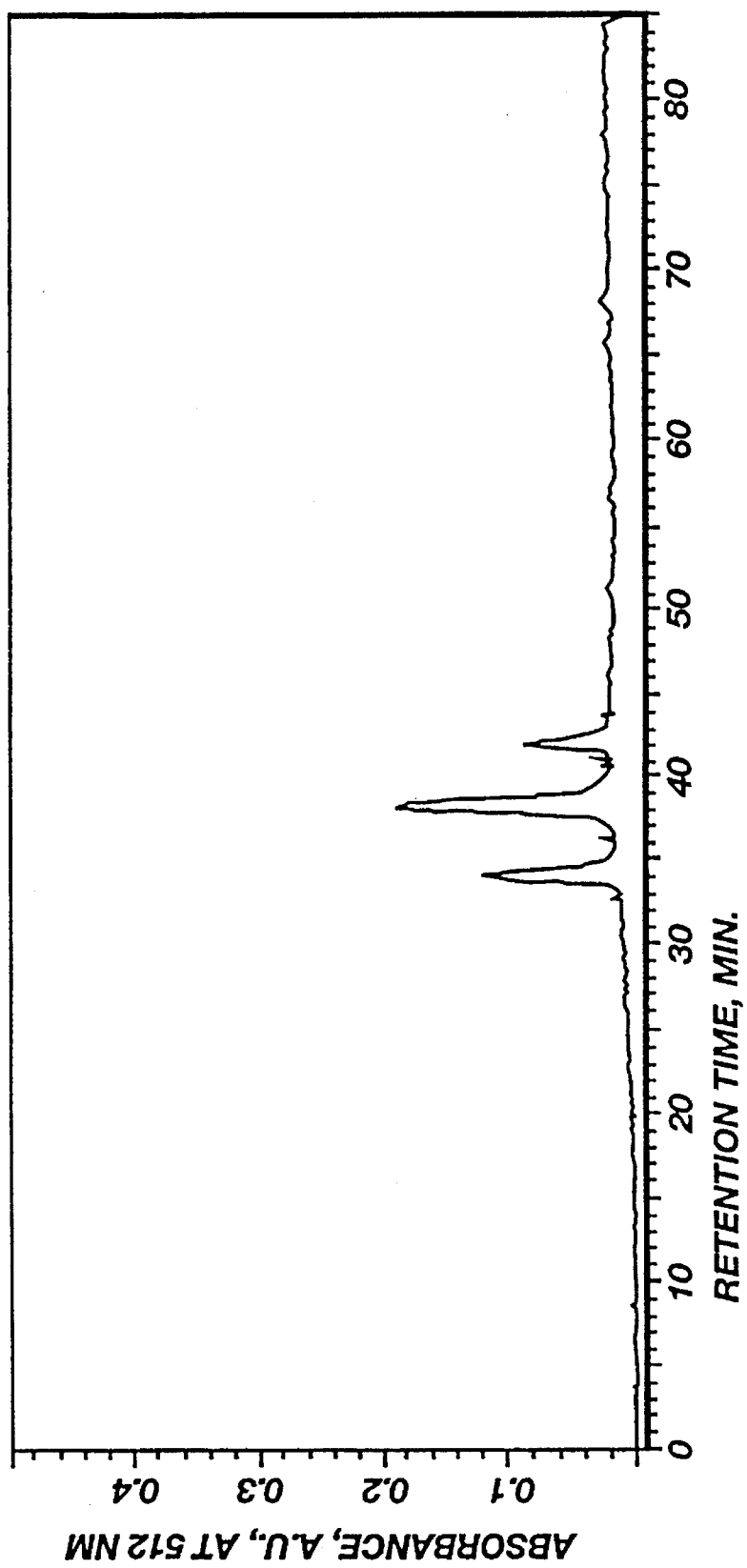

FIGS. 5A, 5B and 6A, 6B depict absorbance chromatograms from high-pressure liquid chromatography (preparative-type column, 25 millimeters by 100 millimeters). In FIG. 5A, absorbance at four different wavelengths is shown: 230 nanometers (abbrev. nm), 280 nm, 360 nm, and 512 nm. Flavonoids and polyphenols are known to have significant absorbance at about 280 nm, with flavonoids also having an absorbance peak at about 360 nm; anthocyanins are known to have significant absorbance of 512 nm light. FIG. 5B is a magnified duplicate of the chromatogram at 512 nm of FIG. 5A. From a comparison of FIGS. 5A and 5B, it can be seen that the peak heights of peaks corresponding to anthocyanin absorbance are about ¹⁄₁₀ or below, the peak heights of peaks corresponding to polyphenol absorbance (280 nm). From the relative peak heights it can be seen that the amounts of anthocyanins in the extract are less than 10% of the amounts of polyphenols. In fact, as the anthocyanin extinction coefficients are much higher than those of polyphenols, the amount of anthocyanins by weight is believed to actually be much lower, possibly as low as 1%.

Twelve fractions 502, 504, 506, 508, 510, 512, 514, 516, 518, 520, 522, 524 were separately collected and further analyzed. Fractions 510, 514, 518, 522 contain significant peaks absorbing at about 350 to about 370 nanometers, wavelengths characteristic of flavonoid and polyphenol moieties. Fractions 504 and 506 span the retention time of anthocyanin peaks absorbing at 512 nm.

Figure 9:
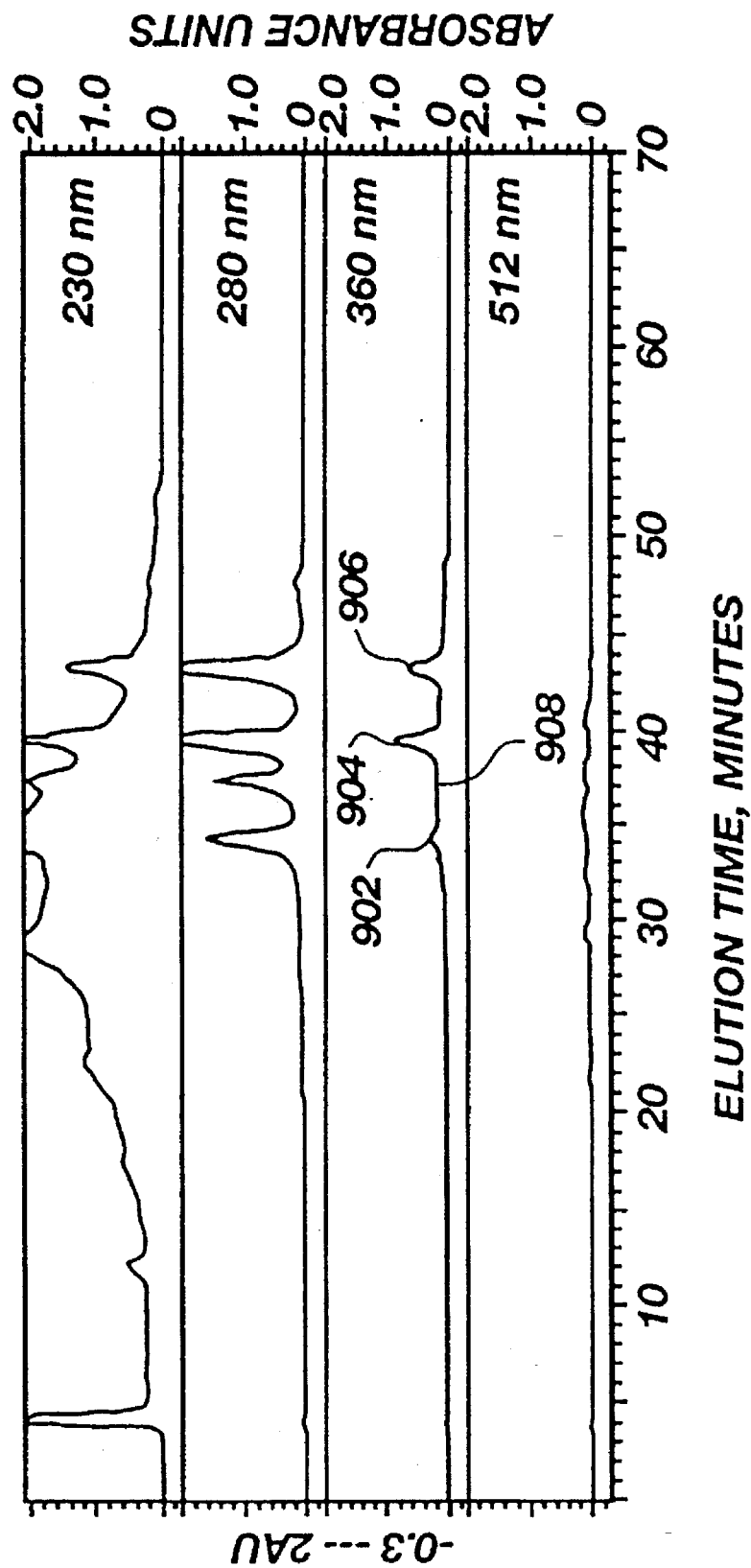
FIG. 9 depicts a chromatogram of the extract obtained with a different column volume than the chromatograms of FIGS. 5A–5B and 6A–6B.

Table V compares the anti-adherence activity of the fraction 502 through 524 with that of a whole (unfractionated) extract. A chromatogram of the latter sample is depicted in FIG. 9 (obtained by the alternative gradient procedure with 50 ml size column). Charts of the absorbance spectrum of fractions 510, 514, 518, 522, 504, and 506 are depicted in FIGS. 7A–7F, respectively.

From these spectra, it is apparent that fractions 510, 514, 518 and 522 all contained relatively large quantities material absorbing at about 350–360 nm. Additionally, as seen in Table V, substantial anti-adhesion activity was found in fractions 504, 506 which did not contain detectable amounts of 360 nm-absorbing material. Fractions 504, 506 contain small amounts of compounds absorbing at 512 nm (which are believed to be anthocyanins), and substantial amounts of material absorbing at 230 to 280 nm. However, a cranberry anthocyanin preparation was analyzed and found not to contain detectable anti-adhesion activity (see Table VI). Thus, it appears that at least some of the cranberry anti-adhesion activity is found in some compounds absorbing at 230 to 280 nm.

The strain of *E. coli* used for the tests on adherence to human bladder

TABLE V

Comparison of HPLC Fractions in Guinea Pig RBC Agglutination Assay

| Fraction # | Activity Index |
| --- | --- |
| 510 | 6 |
| 512 | 4 |
| 514 | 5 |
| 516 | 2 |
| 518 | 1 |
| 520 | 0 |
| 522 | 0 |
| 524 | 0 |
| 526 | 4 |
| 504 | 18 |
| 506 | 18 |
| 508 | 6 |
| 500 | 0 |
| 502 | 5 |
| Step 116 Extract | 9 | cells was isolated from an active bladder infection in a human subject. This strain, designated the #3B strain, appears to possess both type 1 and P-type pili (the latter are sometimes referred to in the research literature as "P-type fimbriae").

Results of the agglutination test for various substances and for the two *E. coli* strains are shown in TABLE VI. Gp indicates guinea pig cell assay; HU indicates human cell assay. In the guinea pig assay, the highest concentration of final extract (step 116) in a 25 μl test dot was 0.056 mg/25 μl; the highest amount of anthocyanins in a dot was 0.063 mg/25 μl; the highest amount of mannose was 0.10 mg/25 μl.

TABLE VI

Comparison of Adhesion Inhibition by Extract to that by Known Substances

| Sample ID | Blood | Activity Index |
| --- | --- | --- |
| 1% mannose | Gp | 24 |
| Final Extract | Gp | 10 |
| EXPT. 1 | Hu | 13 |
| Final Extract | Gp | 9 |
| EXPT. 2 | Hu | 11 |
| Alcohol Extract | Gp | 10 |
| Anthocyanins | Hu | 0 |
| Anthocyanins | Gp | 0 |

Results of a similar test performed on a sample of the acidified alcohol (step 102) extract, with the maximum amount being 0.4 mg/25 μl dot, are also shown. The anthocyanins used in the experiment shown in Table VI were obtained from cranberries by a procedure described subsequently herein and outlined in FIG. 10. In Step 1008B, the elution of the cation column with 1% HCl, after collection of the void volume and aqueous washes (step 1008A), is found to selectively recover much or all of the anthocyanin content of cranberry. The anthocyanin preparation did not contain significant amounts of other substances.

From the results in Tables V and VI, it is apparent that the cranberry extract inhibits both type 1 pili-mediated adhesion of *E. coli* to guinea pig RBCs, and adhesion mediated by P-type pill. Since the extract contains virtually no free monomer or dimer sugars, the inhibition of P-type adhesion cannot be attributed to such sugars. Interestingly, P-type adhesion is believed to occur at high levels in *E. coli* in urinary tract infections.

The extract also reduced the adherence of *Pseudomonas aeruginosa* to bladder epithelial cells, although to a lesser degree than observed with *E. coli*. There was no apparent effect upon the adherence of several Lactobacillus strains to human bladder cells.

Additionally, *E. coli* did not adhere to polystyrene plastic in the presence of the extract. However, it should be noted that in general *E. coli* do not tend greatly to adhere to polystyrene.

An extract having the characteristics of the enriched extract described hereinabove may be prepared by the steps illustrated in FIG. 1. Except for the final non-polar solvent extraction, which selectively removes anthocyanins, this method is similar to a standard method useful to extract anthocyanins from plant materials (see for example *Official Methods Of Analysis of the Association of Official Analytical Chemists*, sections 22.092 through 22.095 et seq., pages 424–425, 1984; also "Purification of Cranberry Anthocyanins", by T. Fuleki and F. J. Francis, *J. Food Science* 33:266–274, 1966.) Anthocyanins are flavonoid compounds closely related to, and often co-isolating with, polyphenol compounds. However, cranberry-derived anthocyanins tested by the methods described hereinabove did not significantly inhibit bacterial adhesion to surfaces. Moreover, cranberry extract which is about 1000-fold enriched for the adhesion-inhibiting activity, has low or no levels of anthocyanins. Anthocyanins characteristically exhibit strong absorption of 512 nanometer light. From the chromatograms of FIGS. 5A and 5B, it is apparent that the levels of anthocyanins in the extract were at least about tenfold lower than the levels of polyphenol components absorbing at about 360 nanometers.

Figure 1:
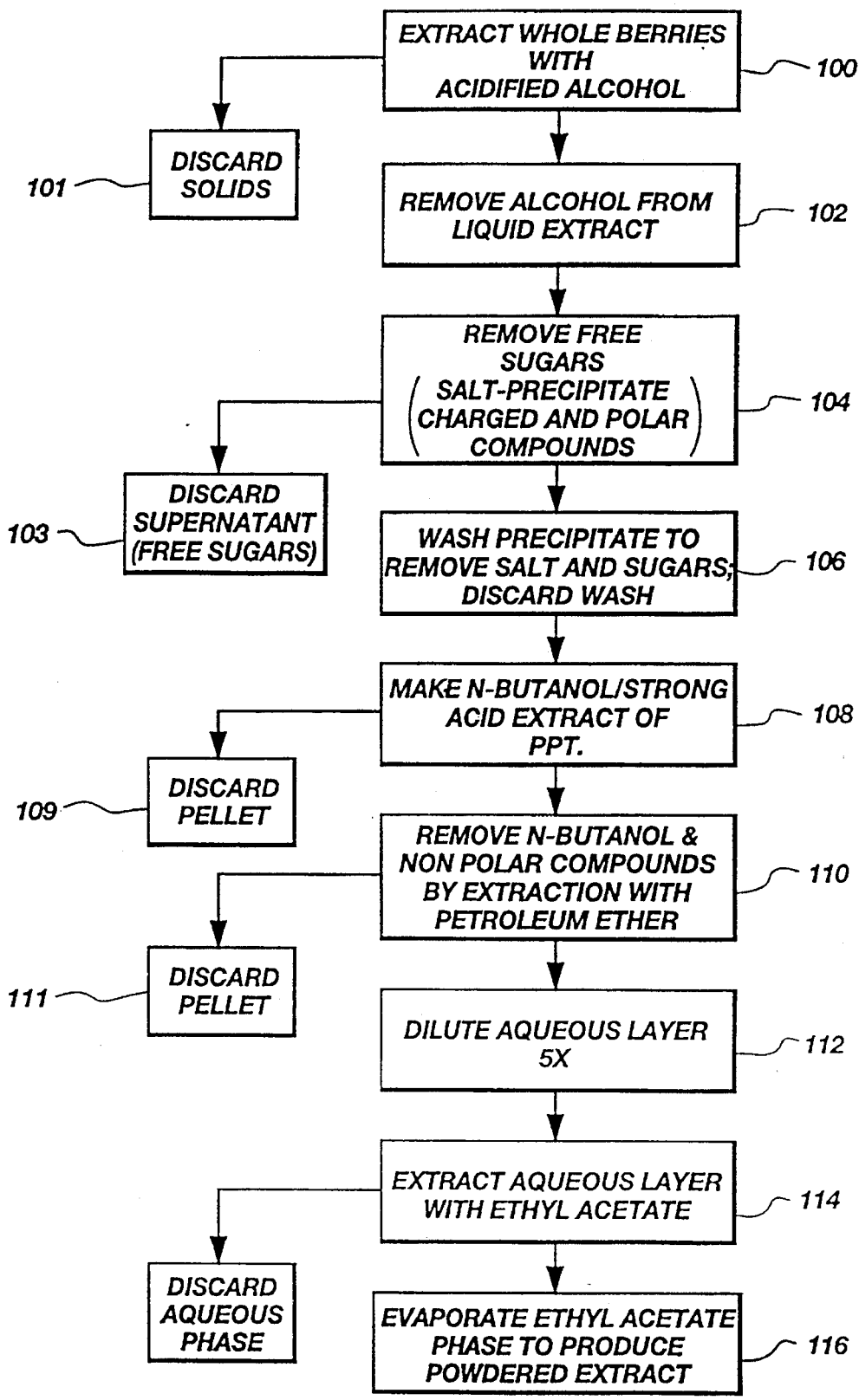
FIG. 1 is a flow chart illustrating the steps of preparation of an extract according to the invention.

The method depicted in FIG. 1 also removes substantially all the simple sugars and most of the benzoic acid from the enriched extract. However, other methods are known for concentration and purification of polyphenols and related compounds such as flavonoids, anthocyanins and catechols from cranberries and other plant materials (see for example G. Puski and F. J. Francis, "Flavonol glycosides in cranberries", *J. Food Science* 32:527–530, 1967; T. Fuleki and F. J. Francis, "Quantitative methods for anthocyanins: purification of cranberry anthocyanins", *J. Food Science* 33:266–274, 1968; P. L. Wang et al., "Isolation and characterization of polyphenolic compounds in cranberries ", *J. Food Science* 43: 1402–1404, 1978; the contents of which are hereby incorporated by reference). Such other methods may also produce an extract enriched for anti-adhesion activity, but having greater or lesser amounts of peripheral substances such as the previously mentioned sugars, benzoic acid, and anthocyanins.

A method for preparing an enriched extract is as follows. First, polar and charged compounds including anthocyanins and other flavonoid and polyphenol compounds are extracted from plant material of plants of the genus Vaccinium (step 100). Preferably, the plant material is berries or fruits. A presently preferred embodiment uses cranberries (*V. macrocarpon*).

In the preferred embodiment, step 100 involves crushing whole cranberries, mixing them with a large volume of acidifed alcohol, and thoroughly agitating the mixture. The acidified alcohol preferably comprises a fairly polar alcohol and water in about equal proportions, with a suitable acid in an amount of about 3 to about 10% by volume. In the presently preferred embodiment, the proportions are 10:1:10 ethanol:acetic acid:water. Suitable alcohols include methanol, ethanol, and propanol, and suitable acids include acetic acid, hydrochloric acid, and phosphoric acid.

Step 100 produces a liquid extract containing mainly polar and/or charged compounds including the active fraction, with a solid residue of berry debris containing largely nonpolar compounds. The solid residue is discarded.

The liquid extract is then concentrated to about 4–6% of the original volume of extract (step 102), with removal of a substantial part of the alcohol. Typically, the extract is evaporated to perhaps about 1–5% of the original volume of liquid extract, and then water is added to make it up to 4–6% of the original volume. The result is a concentrated liquid extract.

Next (step 104), monomer and dimer sugars are substantially removed from the concentrated extract. In the working embodiment, a metal acetate or sulfate, preferably zinc or magnesium acetate or zinc sulfate, is added to the concentrated liquid extract to cause formation of a solid precipitate leaving the simple sugars in solution. The precipitate includes complexes of the active fraction with the metal. Preferably, step 104 is carded out by adding sufficient metal compound to the extract to a concentration of about 1 molar to 1.1 molar, followed by about 0.4 volumes of a volatile inorganic base are added to the concentrated extract and thoroughly mixed. The inorganic base is desirably rather strong; in the illustrated embodiment, ammonium hydroxide is used. Formation of a solid precipitate occurs relatively rapidly upon addition of the base.

Of the metal salts tried, lead acetate produces the greatest enrichment for the active fraction. However, lead acetate may be undesirable depending upon the final use of the product active fraction. For example, trace amounts of lead in a culture vat cleaned with the active fraction might have deleterious effects on subsequent cultures, or end up in food products produced from the cultures. Lead acetate would also be undesirable if the active fraction were to be used in orally ingested compositions, for example a mouthwash for inhibiting bacterial adhesion to teeth, or a health product.

Where the use of a lead compound is undesirable, other metal salts may be used, for example zinc, magnesium, nickelous, barium and calcium, cobalt or sodium acetates, or zinc sulfate. Of these, zinc acetate, magnesium acetate, and zinc sulfate are found to produce the greatest enrichment for the active fraction. Nickelous, barium and calcium acetates produced an enrichment of 60–80% relative to that achieved with zinc acetate (taken as 100%), while sodium acetate and cobalt acetate gave relative yields of only 20–40%.

Desirably, the precipitated solids are washed with a large amount of a polar alcohol such as 80% ethanol in water, to remove excess salt and trace remnants of monomer and dimer sugars (step 106). Methanol or propanol may be substituted for ethanol.

The washed solids are then mixed with n-butanol and concentrated hydrochloric acid, in a proportion of about 6:1

(step 108). The n-butanol removes the metal ion and solubilizes the active fraction, while the hydrochloric acid is believed to alter the relative polarity of the active components to thereby render them soluble in n-butanol. Although n-butanol is presently preferred, other moderately polar solvents such as i-butanol, t-butanol, pentanol or hexanol may be substituted for n-butanol. The result is an alcohol liquid phase and a pellet comprising mostly metal chloride; the pellet is discarded (step 109).

The butanol is then removed from the liquid phase from step 108 by extraction with a nonpolar organic solvent such as petroleum ether (step 110). About three to about ten volumes of the organic solvent are added to the alcohol liquid phase and vigorously mixed, then let stand to allow separation into a hydrophobic first organic phase comprising petroleum ether and butanol, and a first aqueous phase which contains the active fraction. The first aqueous phase, which is generally orange-red to red-brown in color (due at least in part to the presence of anthocyanins), is separated from the organic layer and diluted with about 4 volumes of water (step 112).

Highly desirably, the first organic phase is back-extracted with water (1/20 volume) until all of the red color has been removed from the first organic phase. The water layers from the back-extractions are then combined with the aqueous phase of step 110, before the dilution of step 112 and subsequent steps.

After dilution, the first aqueous phase is then further extracted with a moderately polar organic such as ethyl acetate (step 114) to produce a second organic phase containing the active fraction, and a second aqueous phase in which a substantial proportion of the anthocyanins remains. Preferably, the first aqueous phase is extracted three times sequentially with about an equal volume of ethyl acetate, and the three ethyl acetate phases are pooled. Alternatively, the extraction step 114 may be performed as two sequential extractions, the first with an equal volume of diethyl ether, the second with an equal volume of ethyl acetate.

In either case, following extraction 114 the second organic phase is separated from the second aqueous phase and evaporated to leave a paste or powder which is generally orange in color and having a density of about 0.430 g/cm$^3$. The powder has a solubility in water of about 8.5 grams per milliliter. This product will for convenience be termed a "flavonoid-enriched extract", which is consistent with the spectral data indicating enrichment for flavonoid-containing compounds. However, the term is not intended as limiting the active fraction of the extract to flavonoids or the like. The anthocyanins are substantially selectively retained in the second aqueous phase of extraction 114, although some may remain in the second organic phase. However, the second aqueous phase has considerably less anti-adhesion activity than the second organic phase, indicating that the active fraction probably does not include significant amounts of anthocyanin compounds.

The extract prepared by the process described in the preceding paragraphs is enriched about 1000-fold for an active fraction which inhibits the adhesion of bacteria, including *E. coli* and *Pseudomonas aeruginosa*, to mammalian cells and to certain surfaces. There is no detectable protein, and little or no free monomer and dimer sugars, in the enriched extract. Those free simple sugars remaining are primarily simple reducing sugars such as glucose and fructose. The caloric value of the extract is generally less than about 4 calories per gram. Also, the acid content of the enriched extract, especially the benzoic acid content, is considerably lower than that of Vaccinium berries and of many other cranberry extract or powder products presently known.

EXAMPLE #3

Comparison of extract yields using different metal compounds in Step 104:

Four hundred twenty (420) grams of cranberries were ground with 420 ml of acidified alcohol, and the mixture was let to stand overnight. The mixture was centrifuged, the supernatant #1 separated and set aside, and the solid pellet #1 ground with an additional 1200 ml of acidified alcohol. The ground pellet #1 mixture was centrifuged, the supernatant #2 set aside, and the pellet #2 was in turn ground with 1000 milliliters (abbreviated hereinafter as "ml") of acidified alcohol. The ground pellet mixture #2 was again centrifuged and the supernatant #3 was combined with supernatants #1 and #2.

The combined supernatants were evaporated to a volume of 450 ml having a pH of about 1.7. The mixture was divided into six portions of about 75 ml each. To each of the 75 ml portions, 20 ml of 15 molar ammonium hydroxide was added, bringing the solution to a pH of about 8.5 to 8.8. Individual samples were then respectively mixed with 100 ml of a 1.1 molar solution of one of the following: zinc acetate, zinc sulfate, calcium acetate, barium acetate, cupric acetate, cobalt acetate. The samples were centrifuged, the supernatant discarded, and each pellet was washed three times with 100 ml of 80% ethanol in water each time. The wash supernatants were also discarded.

Next, to each pellet 20 ml of n-butanol and an amount of concentrated hydrochloric acid sufficient to reduce the pH to less than about pH 2.5 was added (step 110; generally about 0.75 ml of HCl with certain exceptions as noted in Table VII. The zinc sulfate-treated sample produced a relatively large pellet to which it was necessary to add an additional 0.8 ml of HCl to achieve satisfactory solubilization of the pellet. For the barium acetate sample, an additional 0.25 ml of HCl was needed to react the pellet. The pH of all the samples ranged between about 0.8 and 2.5.

The six samples were again centrifuged and the pellets discarded. The butanol supernatant of each of the six samples was subjected to petroleum ether extraction (step 112), with a sufficient number of back-extractions with water to transfer essentially all the red color from the organic phase to the aqueous phase. Results of the petroleum ether extraction for the six samples (step 112) are summarized in Table VII.

The aqueous layer of each sample was then extracted 3 times with 50 ml ethyl acetate (Step 114). The zinc acetate-treated sample yielded about 150 ml of orange-red ethyl acetate phase. The zinc sulfate sample yielded about 150 ml of dark red solution. The calcium acetate sample produced about 150 ml of a yellow-orange solution. The barium acetate-treated sample produced about 150 ml of a light yellow solution, while the cupric acetate sample yielded about 150 ml of a intense yellow solution, and the cobalt-treated sample resulted in about 150 ml of a yellow solution.

The separated ethyl acetate phase of each of the samples were evaporated to dryness (except for the zinc sulfate sample, which did not become fully dry), producing a red powdery residue. The recovered weight of the dry extracts was as follows: zinc acetate, 63 mg; zinc sulfate, 2980 mg; calcium acetate, 31 mg; barium acetate, 113 mg; cuptic acetate, 14 mg; cobalt acetate, 26 mg.

TABLE VII

| Sample | Vol. Petr. Ether | No. Back-Extr. | Aqu. End Vol. |
|---|---|---|---|
| EXAMPLE #3 | | | |
| Zinc acetate | 100 ml | 2 | 30 ml |
| Zinc sulfate | 300 ml | 1 | 25 ml |
| Calcium acetate | 100 ml | 2 | 30 ml |
| Barium acetate | 300 ml | 3 | 50 ml |
| Cupric acetate | 100 ml | 2 | 30 ml |
| Cobalt acetate | 100 ml | 2 | 30 ml |
| EXAMPLE #4 | | | |
| Zinc acetate | 100 ml | 3 | 40 ml |
| Nickelous acetate | 100 ml | 3 | 30 ml |
| Magnesium acetate | 100 ml | 3 | 30 ml |
| Sodium acetate | 100 ml | 3 | 25 ml |
| Ammonium acetate | 100 ml | 3 | 20 ml |

EXAMPLE #4

A second comparison of yield using different metal compounds in Step 104 was performed in the same manner as for Example #3. The results are included in Table VII. The dry weight yields were: zinc acetate, 46 mg; nickelous acetate, 14 mg; magnesium acetate, 17 mg; sodium acetate, 18 mg; ammonium acetate, 1 mg.

Figure 8:
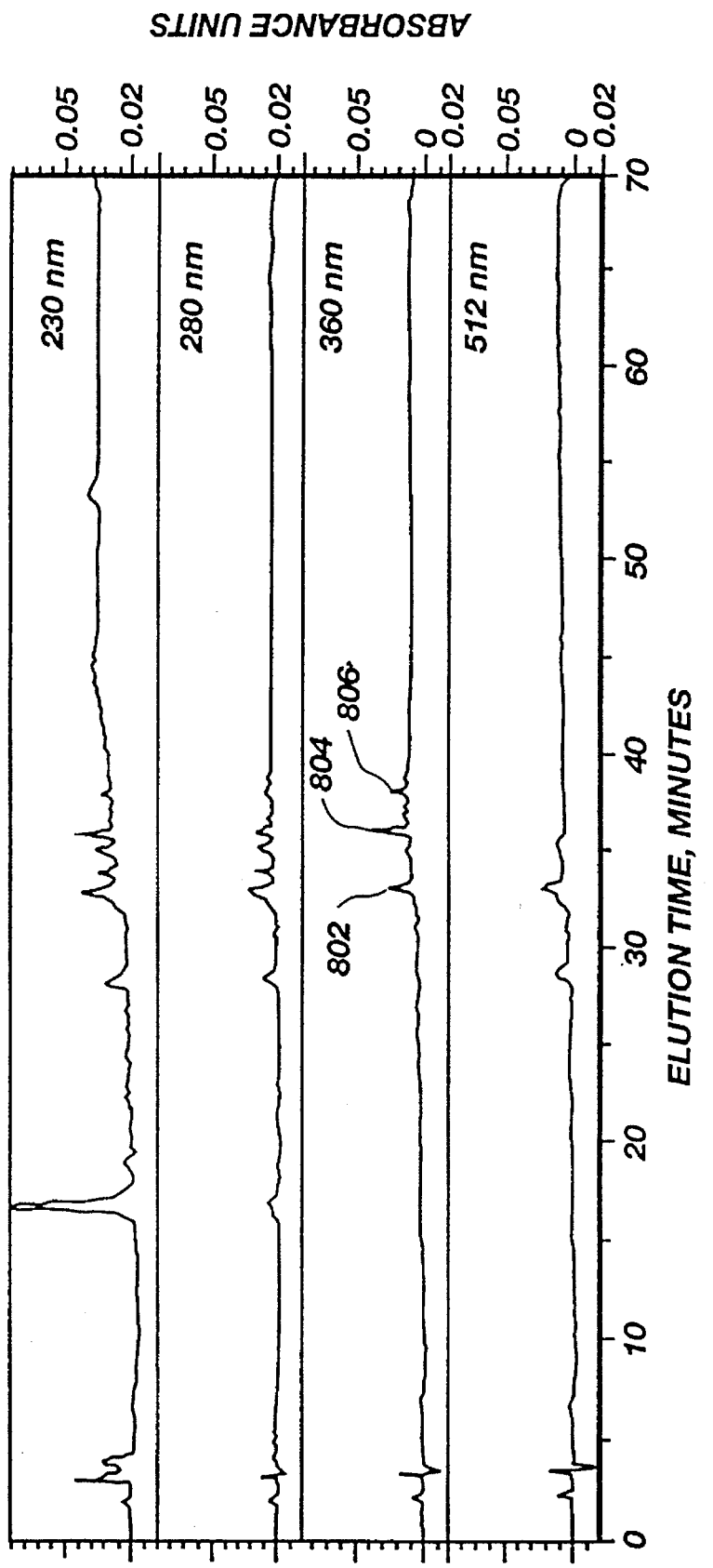
FIG. 8 depicts a chromatogram of a first-step extract of crushed cranberries analyzed at multiple wavelengths.

FIG. 8 shows a chromatogram of the initial liquid extract resulting from step 102, made from cranberries. The liquid extract (the aqueous supernatant after removal of the alcohol) had a volume approximately the same as the starting volume of cranberries (see Example III). The chromatogram of FIG. 8 differs from that of FIGS. 5A, 5B, 6A, and 6B in that a different column size, with 4 μm particle size packing, was used with a slightly different procedure. To obtain the chromatogram of FIG. 8, an analytical C18 column of dimensions 8 millimeters diameter, 100 millimeters length and a volume of 5 ml was used. The concentration by weight of material in the extract was about 200 mg per ml (determined from an aliquot of the liquid extract evaporated to dryness). Fifty microliters (abbrev. μl) of a 200 mg per ml solution (total mass 10 mg) was injected into the column and a flow rate of 1 ml/min was used. Under these conditions, the most prominent elution peaks 802, 804, 806 absorbing at 360 nanometers have retention times of about 33 minutes, 36 minutes and 38 minutes, respectively.

FIG. 9 depicts a chromatogram of the cranberry extract resulting from step 116, eluted by the alternate protocol on a preparative-size (50 ml) C18 column. In this case, 50 μl of a 50 mg per ml solution of the cranberry extract, was injected onto the column (2.5 mg total mass). Three prominent 360 nm-absorbing peaks 902, 904, 906 are also seen in the chromatogram of FIG. 9, having retention times of about 34 minutes, 39 minutes, and 43 minutes.[1] These peaks are slightly shifted from those of FIG. 8, by an amount consistent with the 5-minute difference in timing of the gradient between the analytical column of FIG. 8 and the alternate (shortened) preparative column protocol.

[1] It will be seen that the retention times of the 368 nm-absorbing peaks differ somewhat from those of the chromatograms of FIGS. 5 and 6, which were obtained on preparative-size columns of 25 millimeters diameter, 100 millimeters length, volume 50 ml, also with C18 type particles.

The following computation provides a rough estimate of the relative enrichment for 360-nm absorbing compounds (flavonoids) in the final cranberry extract. The area under the peaks absorbing at 360 nm in FIG. 9 is about 2.6 A.U. (absorbance units), while that for the 360 m-absorbing peaks in FIG. 8 is about 0.12 A.U. Dividing 2.6 by 0.12, and multiplying the result by 4 the factor of the difference in mass applied to the column (4 times as much material loaded for FIG. 8 as for FIG. 9), the enrichment for 360-nm absorbing compounds in the cranberry extract of step 116 over the levels in the initial liquid extract, is seen to be about 87-fold.

From the rough computation and similar rough estimates made from other samples, it appears that the degree of enrichment for 360-nm absorbing compounds (which are presently believed to be polyphenols), is similar to the degree of enrichment for anti-adherence activity in the final cranberry extract.

Further preferred modifications and alternate embodiments of the process and the resulting extract are as follows.

In the process depicted in FIG. 1, it has been found that in the step of ethyl acetate extraction (step 114), a significantly higher yield both in terms of mass and in terms of activity level per unit mass is obtained if the extraction is performed under acidic conditions. Desirably, the extract at this stage has a pH of about 2 or less. If needed, acidification is accomplished by addition of HCl.

A variety of methods may be used to obtain an initial aqueous Vaccinium extract from which the anti-adhesion activity may be obtained. Table VIII includes a comparison of activity obtained using a selection of extraction methods.

Also, it has been found that in lieu of fresh or frozen berries, another useful starting material is an aqueous solution of a powdered cranberry product (commercially available under OCEAN SPRAY brand). This solution may be used in place of the acidified alcohol-water extract of whole berries (steps 100–102 of FIG. 1). The cranberry powder is believed to be obtained by spray-drying of an aqueous extract of the raw cranberry material. A solution of 10% by weight of powdered cranberry is a starting material that has yielded good results. Higher concentrations of this powder may leave some material not fully dissolved. In a procedure starting with such a cranberry solution, the steps 100, 102 of extraction of whole berries and removal of alcohol from the extract are eliminated.

An alternate embodiment (FIG. 10) involves processing the initial aqueous extract largely by chromato-graphic separation steps instead of by precipitations, phase separations etc. This embodiment is presently preferred for convenience and because it reduces the use of organic solvents. However, the chromatographic embodiment is still directed to the fundamental steps of enriching for charged and polar compounds, removing monomer and dimer sugars, removing benzoic acid and other organic acids, and removing anthocyanins, and these steps could be accomplished by substituting the appropriate steps previously described in reference to FIG. 1. That is, a "hybrid" embodiment combining certain steps from the embodiment of FIG. 1 and some from the embodiment of FIG. 10, may also produce the desired extract.

Figure 10:
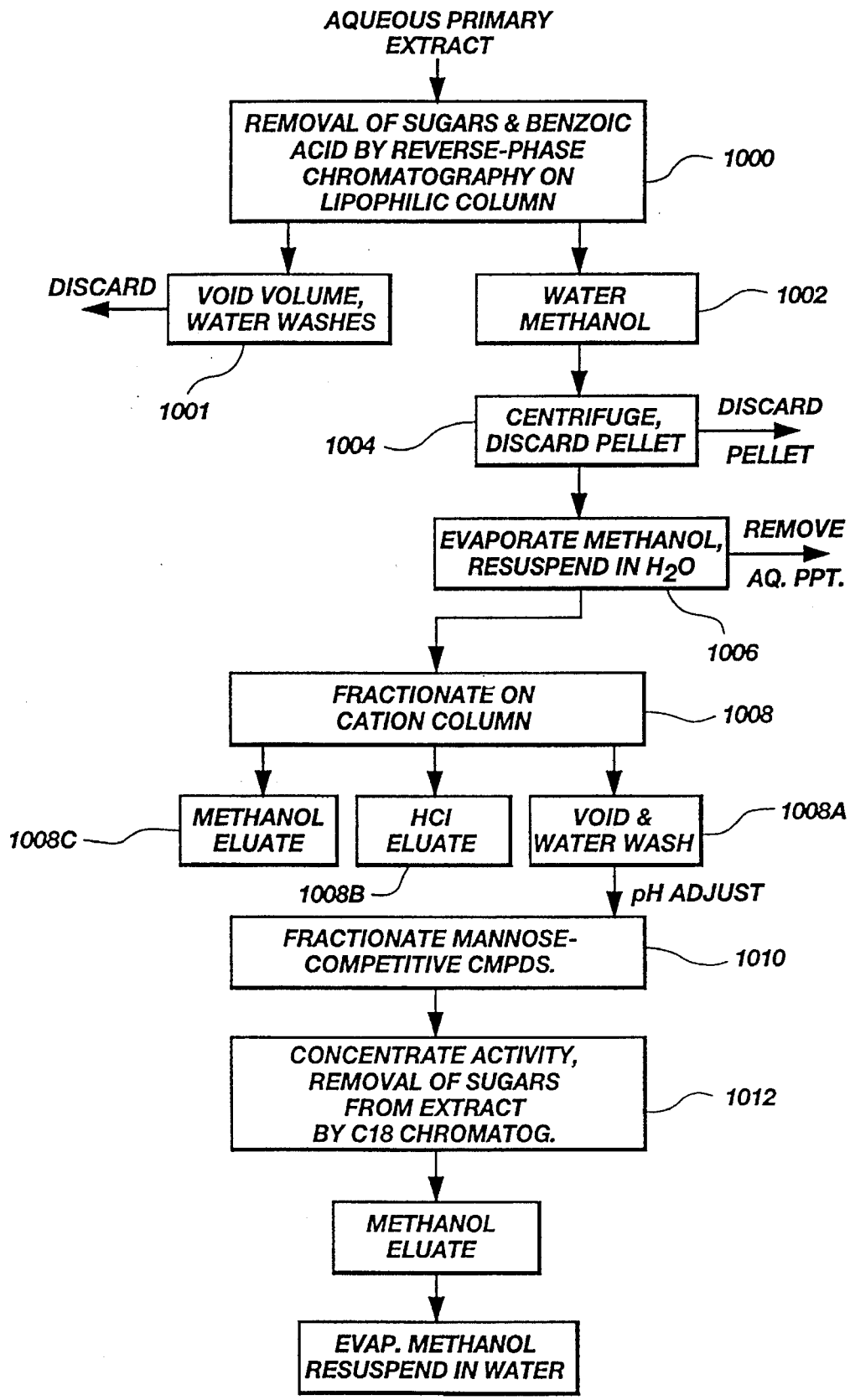
FIG. 10 is a flow chart depicting the steps of an alternate method for preparation of an extract according to the invention.

For example, in the embodiment of FIG. 10, the removal of simple sugars and benzoic acid from the extract (steps 104, 106, 108–111) is accomplished by reverse-phase affinity chromatography on a lipophilic column, such as the C18 also used for HPLC analysis of the extract (step 1000).

The chromatographic embodiment may desirably include a further step of selectively separating compounds which compete with mannose for binding to a mannose-affinic substrate. This step is accomplished by subjecting the extract to affinity chromatography on a mannose-binding substrate bound to a support. In the present working examples, a concanavalin-A (abbreviated conA) column which is commercially available from Sigma Chemical Co. is used. ConA is known to bind mannose, and mannose binds to type 1 pili and interferes thereby with the pili-mediated adhesion of type 1 pili. In the conA affinity chromatographic step, the extract is passed over the column to cause selected components to bind to the conA, and non-conA-binding compounds are washed from the column. A solution containing a sufficient excess of mannose or a mannose derivative is then used to elute the selected components from the column by competition.

It will be apparent that other mannose-binding agents could be similarly used for a mannose affinity chromatography separation. An alternate embodiment presently contemplated involves isolation of the pili and/or the mannose binding region of the pili, and use of this in place of conA for affinity chromatography. However, conA-conjugated supports are presently commercially available and thus convenient.

Highly desirably, the mannose affinity chromatography is performed after the extract has been partially purified by other steps. For example, the extract should already be free of simple sugars, which could bind to conA and thus interfere with the binding of the desired polyphenol and flavonoid compounds.

A presently preferred embodiment of the method for chromatographic preparation of the extract is depicted in FIG. 10. The first step 1000 of the procedure is to remove the monomer and dimer sugars and benzoic acid from a primary aqueous Vaccinium extract, by subjecting the primary extract to reverse-phase liquid chromatography on a lipophilic column. The primary extract can be obtained by making an aqueous solution of a powdered starting material as described above, by making an acidified alcohol extract as by steps 100–102 of the method of FIG. 1, or by other equivalent means.

In a working embodiment, the reverse-phase chromatography of step 1000 is performed on a C18 column (Waters C18 "BondaPak", 10 μm beads, available from Millipore Corp., Waters Chromatography, 34 Maple St., Milford Mass. 01730, cat. # WAT038505). A 50-ml C18 column is prepared essentially according to the manufacturer's directions, by flushing first with 100 ml methanol and then 200 ml distilled water at a flow rate of 4–6 ml/min. From 350 ml to about 500 ml of the aqueous primary extract is then loaded onto the C18 column at a flow rate of 2.0 ml/minute to about 0.5 ml/minute. If the fluid leaving the column during loading becomes pink or red in color, this indicates that the column is being saturated. The column is then washed with an excess of water (800–1000 ml, or a sufficient amount until the eluant appears colorless or hint pink), at a flow rate of about 4–6 ml/min, to remove the sugars. Next, a sufficient volume of methanol, typically about 150 ml to about 300 ml, is run through the column to elute the desired compounds. The methanol eluate should be a deep red; when the eluate becomes pale pink then sufficient methanol has been passed through the column. The methanol eluate usually contains precipitate which is readily removed by centrifugation at 1500 to 5000 rpm with a tabletop or slightly larger centrifuge (step 1004). The precipitate is discarded and the desired activity is found in the supernatant.

The methanol supernatant of step 1002 is then evaporated under vacuum to evaporate all of the methanol, and redissolved in about 25 ml warm water, preferably with sonication (step 1004). The sample is filtered with a Whatman #1 filter to remove precipitate, which is discarded.

The aqueous sample is then subjected to chromatographic separation on a cation column (step 1008). A 4 ml to 8 ml cation column is prepared as generally known, from a slurry of cation material in water. A presently preferred cation material is the Waters Accell+CM Cation, which is a silica bead with a hydrophilic bonded layer having carboxymethyl as the available cation group (Millipore Corp., Waters Chromatography, 34 Maple St., Milford Mass. 01730). In a typical procedure, the aqueous sample which has a volume of about 5 ml is carefully loaded directly onto the cation column. At this point, a green color will be observed in the column and a very dark green material at the top of the column. The column is then washed with about 25 ml of distilled water (step 1008A). The dark green material at the very top washes out only very slowly with plain water, and is desirably left behind.

The initial loading solution and the water wash (the void volume; step 1008A) of the cation column contain a substantial amount of the desired anti-adhesion activity. A substantial portion of anthocyanins are removed from the extract by the cation column, as revealed by analytic C18 chromatography of products 1006 and 1008A (also subjected to the optional $CHCl_3$/EtAc extraction). Desirably, the column is now washed with 1–2 volumes of 1% hydrochloric acid (step 1008B), which elutes essentially all the green material. The HCl eluate has been found to consist mostly of anthocyanins. Following the HCl elution, a step of methanol elution (step 1008C) is then performed. The methanol eluate 1008C, upon evaporation and resuspension in water, is surprisingly found to contain a substantial amount of anti-adhesion activity. The methanol eluate compound(s) have significant HPLC elution peaks observable by absorbance at 230 nm, 280 nm and 360 nm.

The void volume eluate 1008C is then concentrated by evaporation to a concentration of less than about 60 mg/ml, in preparation for affinity chromatography on a concanavalin A column (conA). A 3 ml to 10 ml column of conA-bound column material (commercially available from Sigma, St. Louis Mo., cat. #C-9017) is prepared and flushed with 100 ml of phosphate buffer (0.05M sodium phosphate, adjusted to pH 7 with phosphoric acid) at a flow rate of about 1 ml/minute. Two ml of the aqueous eluate, containing no more than 60 mg/ml sample, is adjusted to the same concentration of conA phosphate buffer and applied to the column. After loading, the column is washed with about 50 ml of phosphate buffer or until the eluate is clear, again at about 1 ml/minute. Finally, the column is eluted with at least 50–100 ml of phosphate buffer containing 10% α-methyl-mannopyranoside. The mannopyranoside compound is preferred over mannose for this purpose because it binds more tightly to the conA, and thus is expected to more effectively elute compounds bound to the mannose-affinic site on concanavalin A. A 10% concentration of α-methyl-mannopyranoside is found to be more efficient at eluting the active fraction, than a lower concentration of 2%.

The resulting conA-eluate is then subjected to another separation on a C18 column similar to step 1000, to remove the α-methyl mannopyranoside. However, a smaller C18 column (Waters $C_{18}$ Sep-Pak, 1 ml volume, Millipore Corp., Waters Chromatography Division, 34 Maple St., Mifford Mass.; cat. # WAT051910) is sufficient with the more purified sample at this stage. This step also serves to concentrate the active fraction. The column is prepared by passing 5–10 ml methanol followed by 5–10 ml water over it before loading with the 50 ml of conA eluate. The column is then washed with 10–20 ml water, and the active fraction is eluted in a volume of about 2 ml methanol. The sample may be evaporated to dryness and resuspended in a volume of about 150 μl of distilled water.

The resulting extract is pale yellow to brown, indicating that it contains little or no anthocyanins. A large part of the anthocyanins are lost in the cation column separation.

Optionally, a step of extracting the aqueous sample with an equal volume of a moderately polar organic solvent, preferably 50:50 CHCl₃/ethyl acetate, may be introduced into the procedure of FIG. 10. This step is performed to remove some nonpolar or less polar compounds from the extract. Chloroform-EtAc extraction may be performed either after step 1004, or prior to steps 1000, 1002, e.g. on the initial aqueous extract.

The chloroform-EtAc extraction appears to remove a component of the extract which masks or otherwise interferes with the activity of the anti-adhesion fraction in the RBC assay, since its removal generally enhances the activity as measured in that assay without significantly changing the mass yield. However, removal of the apparent "masking" component(s) may decrease the long-term stability of the active compound. Thus, the step of chloroform/ethyl acetate extraction should be employed when attempting to quantitate anti-adhesion activity in the RBC assay, but it may be undesirable to include this step in routine production of the extract.

In performing the chloroform/ethyl acetate extraction, the aqueous sample is preferably extracted twice (each time with an equal volume of chloroform/ethyl acetate). The organic phase(s) are discarded, and the aqueous phase is concentrated by evaporation to about ⅕ its original volume (e.g., around 5 ml). The evaporation also removes trace amounts of the organic solvents. Alternatively, the sample can be evaporated to dryness and resuspended in water. Either way, the resulting aqueous sample is then further purified by step 1008 or step 1004.

Table VIII shows the relative adhesion-inhibiting activity measured for extracts at selected stages in the process of FIGS. 1 and 10, as measured in the red blood cell agglutination assay (abbreviated RBC assay; see Example 2 and Table VI) is given. The activity values are normalized to the activity of a 1% mannose solution in the assay and to the amount of material in grams per milliliter. The mannose solution is 1% or 1 g/100 ml, so a value of 100 indicates activity equivalent to mannose. Values>100 indicate that the sample is more effective than mannose in anti-adhesion activity. The concentrations of the test extracts were determined by weighing portions evaporated to dryness.

The results shown in Table VIII demonstrate that in general different methods of producing the initial extract were comparable, with the MAW, water (room temperature) and boiling water extracts being slightly better in terms of recovery of activity. The 10% solution of Ocean Spray powder was comparable to these as well. To estimate the amount of activity remaining in the pulp, the pulp was extracted with methanol and the methanol-soluble material was prepared in aqueous At present, the MAW (methanol:acetic acid:water) extract is preferred,

TABLE VIII

Anti-Adhesion Activity of Selected Products During Preparation of Extract

| Sample | Normalized activity | |
|---|---|---|
| 1. MAW initial extract | 14.9 | |
| 2. --ppt. from initial extract | 1.2 | |
| 3. Prior to EtAc extraction (step 110, FIG. 1) | 5.7 | |
| 4. Step 114, aqueous phase | 8.4 | (16.8, 0.0) |
| 5. Step 116 (evap. organic phase) | 33.8 | (117.7, 0.0) |
| 6. EtAcEt¹ 10:1:5 initial extract | 4.3 | |
| 7. --ppt. from initial extract | 3.9 | |
| 8. EtAcEt 5:1:10 initial extract | 0.0 | |
| 9. --ppt. from initial extract | 7.7 | |
| 10. Ethyl acetate initial extract | 3.3 | |
| 11. ---ppt. from initial extract | 6.4 | |
| 12. Boiling water | 6.1 | |
| 13. ---ppt. from initial extract | 5.3 | |
| 14. ---Step 1002 product | 23.9 | |
| 15. Refluxed water | 4.1 | |
| 16. ---ppt. from initial extract | 6.6 | |
| 17. ---Step 1002 product | 39.4 | |
| 18. 10% Ocean Spray powder | 4.6 | |
| 19. Step 1001 wash discard | 4.1 | |
| 20. Step 1001, 2nd wash discard | 0.0 | |
| 21. Step 1002 product | 34.5 | |
| 22. CHCl₃/EtAc extract of 1002 prod. | 22.7 | |
| 23. Step 1008A product | 45.1 | |
| 24. Step 1008B HCl eluate | 0.0 | |
| 25. Step 1008C methanol eluate | 92.1 | |

¹EtAcEt = ethyl acetate/acetic acid/ethanol as it appears to result in a greater recovery of activity in the initial extraction from berries and to leave a smaller proportion of activity in the pulp.

Figure 11A:
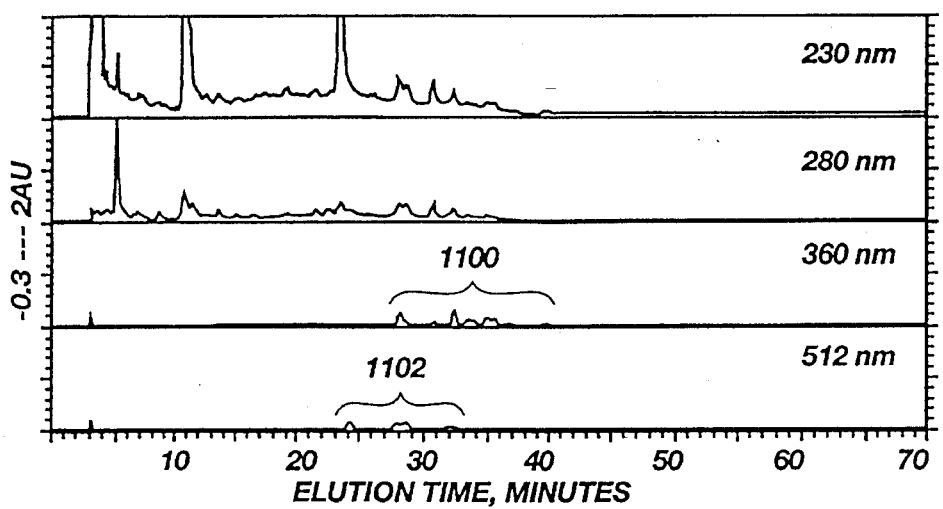
FIGS. 11A–11F are HPLC chromatograms of products of selected steps in the process of the invention.
Figure 11B:
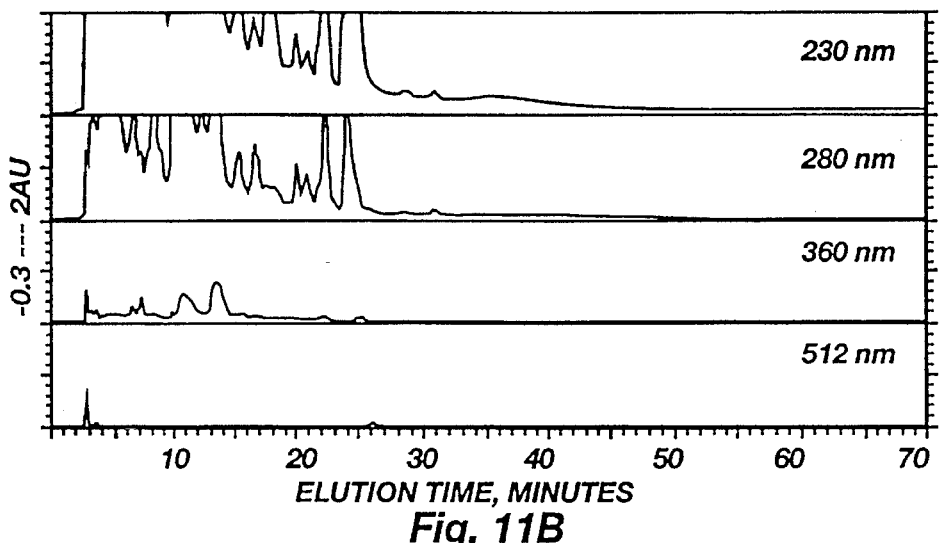
Figure 11C:
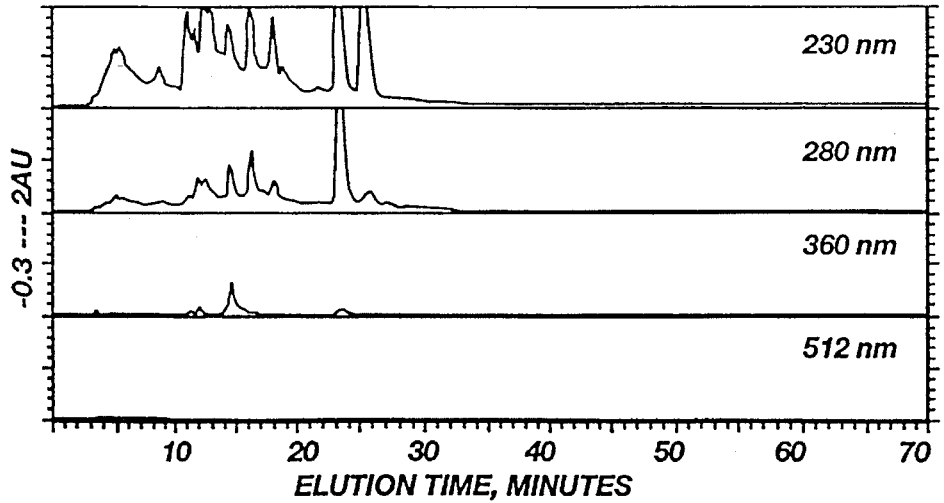
Figure 11D:
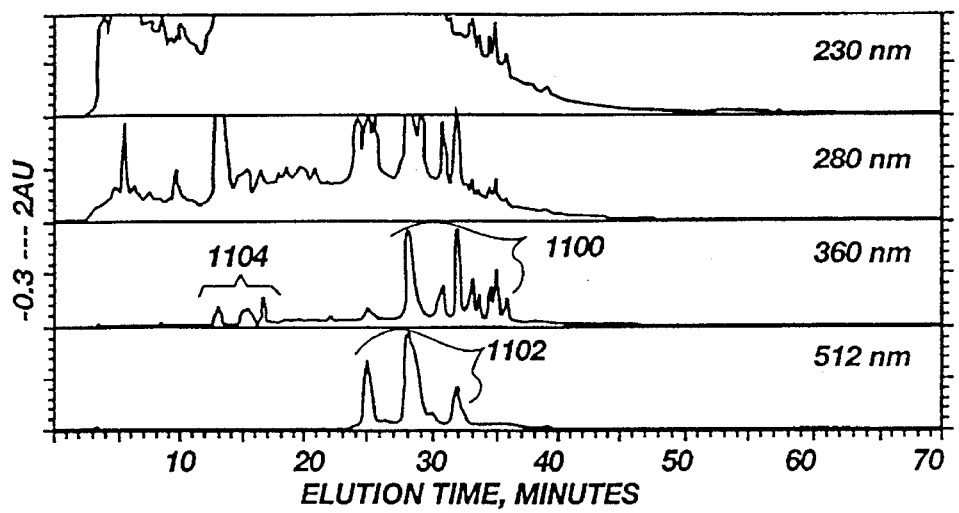

FIGS. 11A–F are chromatograms on a C18 column of selected preparations including some from Table VIII. FIG. 11A is a chromatogram of sample #17 in Table VIII, which is a 10% solution of Ocean Spray powder. FIGS. 11B,C are chromatograms of the water washes of the C18 column from step 1000, corresponding to samples #18, #19 in Table VIII. FIG. 11D is a chromatogram of the methanol eluate from step 1000 containing the active fraction and corresponding to sample #20 in Table VIII. In FIG. 11D a group of 360 nm-absorbing peaks 1100 eluting at between 30 and 42 minutes can be seen. This group of peaks is not detectable in FIGS. 11B or 11C, and the relative amount of material eluting in these peaks is much less in the starting material (FIG. 11A). A group of elution peaks 1102 absorbing at 512 nm, characteristic of anthocyanins, is also seen in FIG. 11D.

Figure 11E:
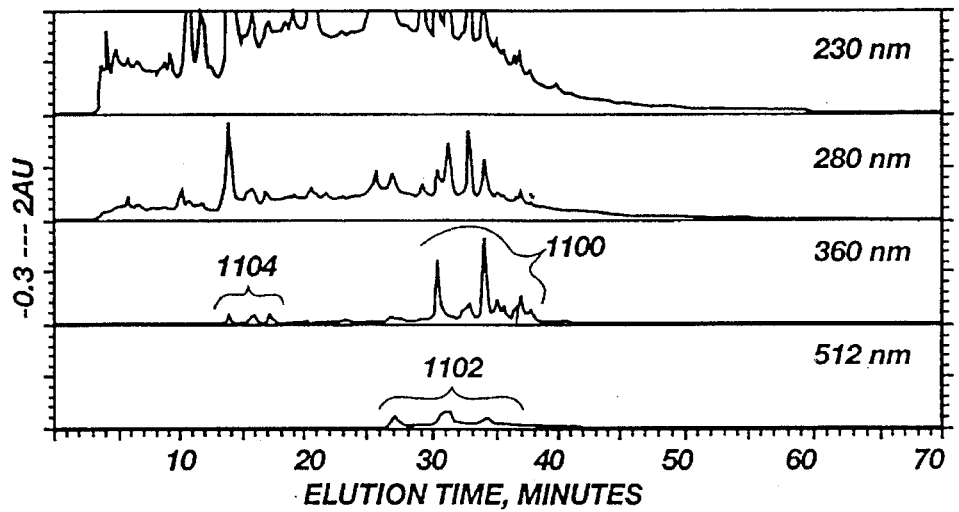
Figure 11F:
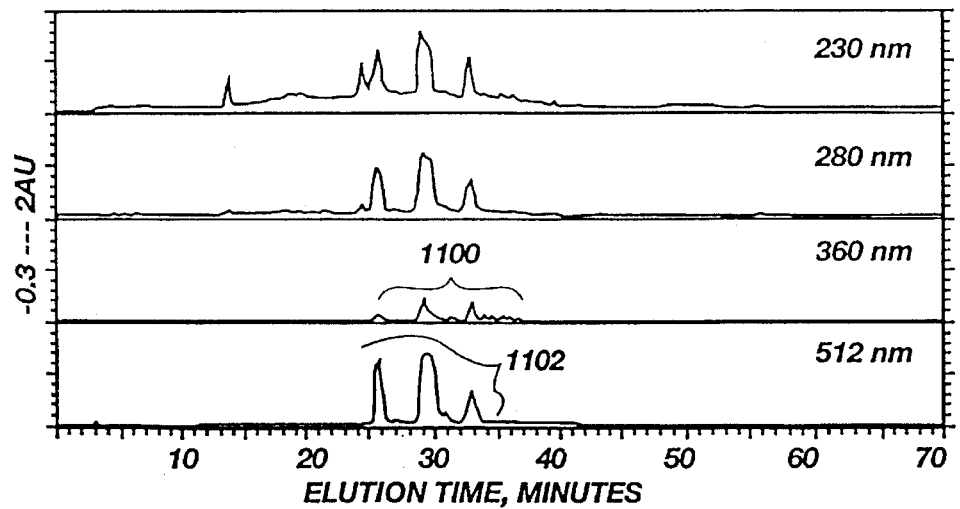

FIG. 11E is a chromatogram of a sample which has been further subjected to cation chromatography, step 1008, corresponding to sample #22 of Table VIII. Peaks 1100 are still present in amount similar to that of FIG. 11D, but peaks 1102 (the anthocyanins) are considerably reduced in amount. Additionally, a group of small peaks 1104 eluting at about 23 to about 27 minutes is detectable. FIG. 11F is a chromatogram of an HCl eluate of the cation column, corresponding to sample #23. Peaks 1102 are present in substantial amount, while peaks 1100 are nearly absent.

Comparison of the RBC assay values and the chromatograms for the samples of FIGS. 11A–11F reveals that the presence of significant activity in the RBC assay is positively correlated with the presence of peaks 1100.

Figure 12:
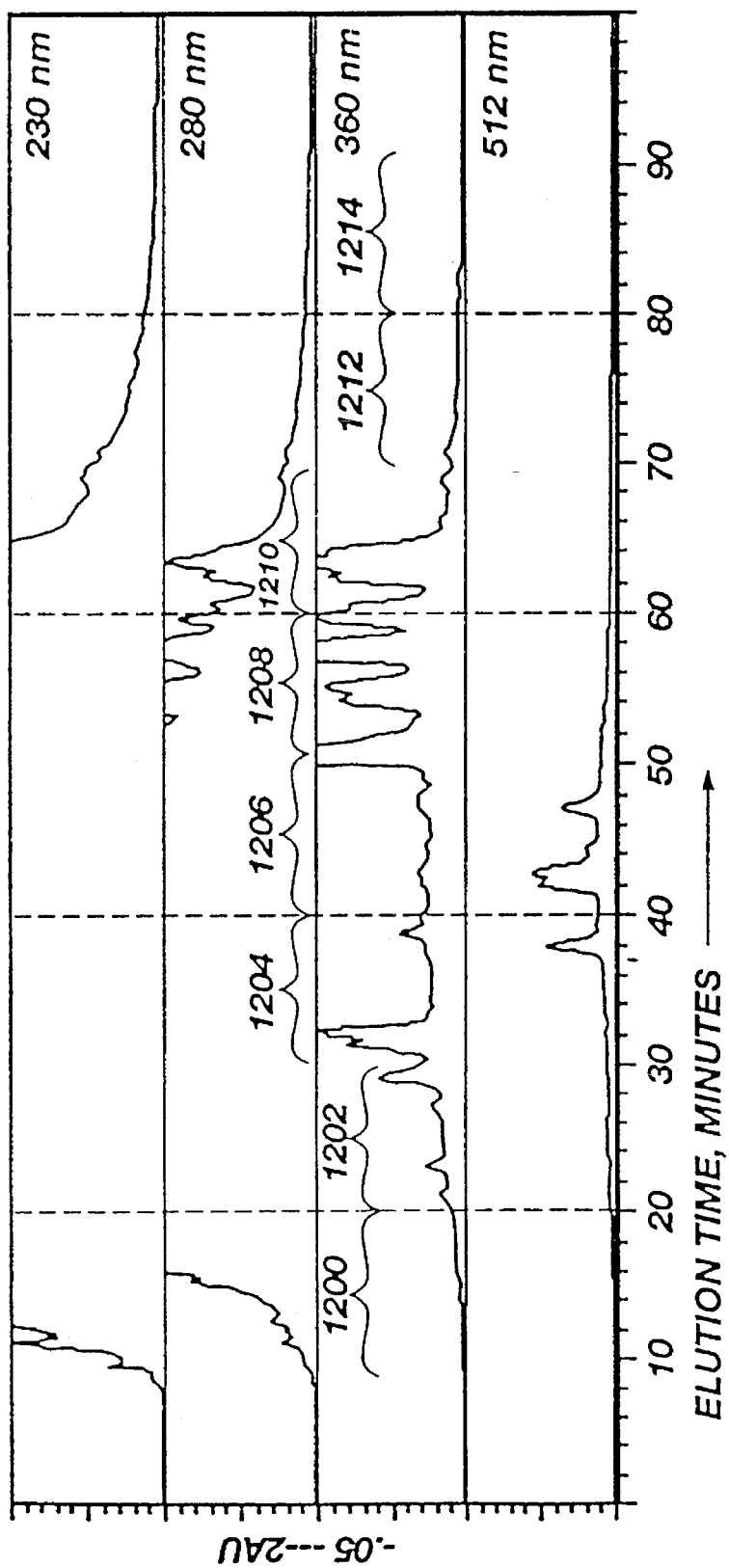
FIG. 12 is a chromatogram of a product of step 1002 indicating collection of sequential fractions for activity analysis.

A sample of the product of step 1008 in the process of FIG. 10 was subjected to HPLC on a large (50 ml) C18 column (FIG. 12). The indicated fractions 1200, 1202, 1204, 1206, 1208, 1210, 1212, 1214 were collected and analyzed in the RBC assay (Table IX). Since fractions 1200–1208 all contained significant levels of activity, it appears that the extract may contain multiple components contributing anti-adhesion activity. From the data it also appears that tannin or tannin-like compounds

TABLE IX

Comparison of Activity in Selected HPLC Fractions

| Sample | Normalized Activity |
|---|---|
| 1200 | 10.5 |
| 1202 | 25.1 |
| 1204 | 37.8 |
| 1206 | 45.1 |
| 1208 | 41.6 |
| 1210 | 0.0 |
| 1212 | 0.0 |
| 1214 | 0.0 | contribute anti-adhesion activity to the extract. Tannins absorb UV wavelengths strongly (at 230 nm and 280 nm). Fractions 1200, 1202 and 1204, which have little material absorbing at 360 nm, have significant elution peaks of material absorbing at 230 and 280 nm, in the wavelength range expected for tannins. It is known that tannins may be retained on lipophilic columns similar to the C18. Thus one might expect an extract produced by the process to include tannin components. Portions of fractions 1200, 1202, 1204, 1206, 1208 were re-run on analytic C18 columns; the results are shown in FIGS. 13A–E.

As shown in the disclosed embodiments and Table VIII, an initial acid extraction of the berries or plant material solubilizes the active fraction. However, in an alternate embodiment, the plant material may be first extracted with a basic solution (high pH) which will result in much of the active compounds being left in the pulp or residue. The pulp or residue itself is thus enriched for the anti-adhesion activity. Such a "reverse" approach for enrichment of a substance known to be acid-soluble, is well known in the art. The pulp or residue can then be further processed by one or more of the steps disclosed in FIGS. 1 and 10 to obtain a more pure preparation of the active fraction. The observed property of acid solubility/base insolubility of the active fraction may also be exploited in other ways to produce an extract or composition highly enriched for the active fraction, as will be apparent to one skilled. For example, a sufficient amount of a base can be added to a partially enriched acid extract to selectively precipitate the active fraction.

A method of inhibiting the adhesion of bacteria to surfaces comprises the steps of providing a Vaccinium extract enriched for anti-adherence activity and for 360 nm-absorbing polyphenol compounds, and applying an effective amount of a composition comprising the extract in an acceptable carrier, to a surface having bacteria such as *E. coli* adhered thereto to disengage the bacteria from the surface. Desirably, the surface is rinsed to remove the disengaged bacteria. The method is useful to inhibit the adhesion of bacteria to such surfaces as teeth, other bacteria adhered to teeth, to human oral epithelial cells, human epithelial urinary tract cells; and to clean dental implants, bacterial fermentation vats, and the like.

The invention is described with reference to specific embodiments, plant species and parts, buffers and chemical procedures and the like. However, it will be recognized by those skilled in the art that various substitutions can be made without departing from the spirit and scope of the invention. In particular, it is known that polyphenols including flavenoids and anthocyanins can be isolated and/or partially purified from plant materials by a number of different methods. It will further be recognized that these alternate methods, and consequent changes in other steps of the method including removal of sugars, of various solvents, and of anthocyanins from a composition comprising partially purified polyphenols, fall within the scope of the present invented Vaccinium extract.

What is claimed is:

1. A composition for inhibiting the adhesion of *E. coli* bacteria to surfaces in a mammalian oral cavity, comprising:

an extract prepared from whole cranberries and enriched by fractionating on a cation column to selectively enrich said extract with respect to flavonoid and polyphenol compounds so that the amount of anthocyanins in said extract is less than about one-tenth the combined amounts of polyphenol and flavonoid compounds in said extract; and an aqueous or aqueous-alcohol liquid medium suitable for rinsing of a mammalian oral cavity.

* * * * *

UNITED STATES PATENT AND TRADEMARK OFFICE
CERTIFICATE OF CORRECTION

PATENT NO. : 5,474,774

DATED : December 12, 1995

INVENTOR(S) : Walker et al.

It is certified that error appears in the above-indentified patent and that said Letters Patent is hereby corrected as shown below:

In Title Page, line [75], change inventor "Mikelsen" to --Mickelsen--;

In Column 7, line 55, insert a space between "508," and "510,";

In Column 9, line 11, change "pill" to --pili--;

In Column 10, line 32, before "The" insert --The supernatant containing the bulk of sugars is discarded (step 103).--;

In Column 12, line 66, change "cuptic" to --cupric--;

In Column 13, line 67, change "m-absorbing" to --nm-absorbing--;

In Column 15, line 50, change "hint" to --faint--;

In Column 16, line 58, change "Mifford" to --Milford--;

In Column 17, line 54, insert --form.-- after "aqueous";

In Column 19, line 24, delete "; the results are shown in FIGS. 13A-E"; and

In Column 19, line 33, delete comma after "soluble".

Signed and Sealed this

Fourteenth Day of May, 1996

Attest:

BRUCE LEHMAN

Attesting Officer

Commissioner of Patents and Trademarks